United States Patent [19] [11] Patent Number: 5,049,548
Greenlee et al. [45] Date of Patent: Sep. 17, 1991

[54] RENIN-INHIBITORY DI-, TRI-, AND TETRAPEPTIDES

[75] Inventors: William J. Greenlee, Teaneck; Jan ten Broeke, Somerset, both of N.J.

[73] Assignee: Merck & Co., Inc., Rahway, N.J.

[21] Appl. No.: 319,448

[22] Filed: Mar. 3, 1989

[51] Int. Cl.$^5$ .................. A61K 37/02; C07K 5/06; C07K 5/08; C07K 5/10

[52] U.S. Cl. .................. 514/18; 514/19; 530/330; 530/331; 546/133

[58] Field of Search .................. 544/58.4, 58.2, 168; 514/18, 11, 19; 530/330, 331; 546/133

[56] References Cited

U.S. PATENT DOCUMENTS 4,748,155 5/1988 Sisto et al. .................. 514/18
4,812,442 3/1989 Boger et al. .................. 544/168

FOREIGN PATENT DOCUMENTS 0081783 6/1983 European Pat. Off. ............ 530/331

OTHER PUBLICATIONS

Chorev et al., "Partially Modified Retro-Inverso Peptide Analogs", Chem. Abstracts, vol. 105, 108710g, 1986.
Burger, *Medicinal Chemistry*, 2nd Ed., 1960, pp. 565–571, 579–581, 600–601.
Denkewalter et al., *Progress In Drug Research*, vol. 10, 1966, pp. 610–612.
Plattner et al., *J. Med. Chem.*, 1988, 31(12): 2277–2288.
Bolis et al., *J. Med. Chem.*, 1987, 30(10): 1729–1737.
Haber, et al., *J. Cardiovasc. Pharmacol.*, 1987, 10(Suppl. 7): 554–558.

*Primary Examiner*—Lester L. Lee
*Assistant Examiner*—Stephen B. Maebius
*Attorney, Agent, or Firm*—Mark R. Daniel; Hesna J. Pfeiffer

[57] ABSTRACT

Renin-inhibitory di-, tri-, and tetrapeptides of the formula I:

A-B-E-G-T-J in which
A is heterocyclic, substituted heterocyclic etc;
B is —N(A$^1$)CH[(CH$_2$)$_2$R$^3$]CO—,
E is absent or is —N(A$^2$)CH[(CH$_2$)$_2$R$^4$]CO—;
G is

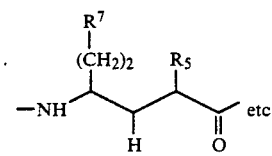

and
J is —Y—(CH$_2$)$_x$[CH(R$^5$)]$_y$—(CH$_2$)$_z$—R$^{10}$ and pharmaceutically acceptable salts thereof are disclosed. These compounds inhibit renin and are useful for treating various forms of renin-associated hypertension, hyperaldosteronism and congestive heart failure; compositions containing these renin-inhibitory peptides, optionally with other antihypertensive agents; and methods of treating hypertension, hyperaldosteronism or congestive heart failure or of establishing renin as a causative factor in these problems which employ these novel peptides.

4 Claims, No Drawings

RENIN-INHIBITORY DI-, TRI-, AND TETRAPEPTIDES

The present invention is concerned with novel di-, tri- or tetrapeptides which inhibit the angiotensinogen-cleaving action of the proteolytic enzyme, renin, with pharmaceutical compositions containing the novel peptides of the present invention as active ingredients, with methods of treating renin-associated hypertension, hyperaldosteronism, and congestive heart failure, with diagnostic methods which utilize the novel peptides of the present invention, and with methods of preparing the novel peptides of the present invention.

BACKGROUND OF THE INVENTION

Renin is an endopeptidase (molecular weight about 40,000) produced and secreted by the juxtaglomerular cells of the kidney. Renin has a high specificity for and cleaves the naturally-occurring plasma glycoprotein, angiotensinogen, at only the 10, 11 peptide bond, i.e., between the 10th (Leu) and 11th (Leu) amino acid residues in the equine substrate, as described by Skeggs et al, *J. Exper. Med.* 1957, 106, 439, or between Leu 10 and Val 11 in the human renin substrate, as elucidated by Tewksbury et al., *Circulation* 59, 60, Supp. II: 132, October 1979.

This cleavage of its tetradecapeptide substrate, angiotensinogen, by renin splits off the decapeptide, angiotensin I, which is thought to be hemodynamically-inactive, but which is converted in the lungs, kidney or other tissue by angiotensin-converting enzyme (ACE) to the potent pressor octapeptide, angiotensin II. Angiotensin II then causes constriction of the arterioles and is also believed to stimulate release of the sodium-retaining hormone, aldosterone, from the adrenal gland, thereby causing a rise in extra-cellular fluid volume. Thus, the renin-angiotensin system plays an important role in normal cardiovascular homeostasis and in some forms of elevated blood pressure (hypertension).

Inhibitors of angiotensin I converting enzyme have proven useful in the modulation of the renin-angiotensin system. Consequently, specific inhibitors of the catalytic and rate-limiting enzymatic step that ultimately regulates angiotensin II production, the action of renin on its substrate, have also been sought as effective investigative tools, as well as therapeutic agents in the treatment of hypertension and congestive heart failure.

Renin antibody, pepstatin (another aspartic proteinase, like renin), phospholipids, and substrate analogs, including tetrapeptides and octa- to tridecapeptides, with inhibition constants ($K_i$) in the $10^{-3}$ to $10^{-6}$M region, have been studied.

Umezawa et al., in *J. Antibiot. (Tokyo)* 23: 259-262, 1970, reported the isolation of a peptide, pepstatin, from actinomyces that was an inhibitor of aspartyl proteases such as pepsin, cathepsin D, and renin. Gross et al., *Science* 175: 656, 1972, reported that pepstatin reduces blood pressure in vivo after the injection of hog renin into nephrectomized rats. However, pepstatin has not found very wide application as an experimental agent because of its limited solubility and its inhibition of a variety of other acid proteases in addition to renin.

Many efforts have been made to prepare a specific renin inhibitor based on pig renin substrate analogy, since such analogy has been shown to correlate well with and predict human renin inhibitor activity. The octapeptide amino acid sequence extending from histidine-6 through tyrosine-13

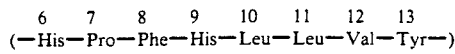

has been shown to have kinetic parameters essentially the same as those of the full tetradecapeptide renin substrate.

Kokubu et al., *Biochem. Pharmacol.*, 22, 3217-3223, 1973, synthesized a number of analogs of the tetrapeptide found between residues 10 to 13, but while inhibition could be shown, inhibitory constants were only of the order of $10^{-3}$M. Analogs of a larger segment of renin substrate have been also synthesized, e.g., Burton et al., *Biochemistry* 14: 3892-3898, 1975, and Poulsen et al., *Biochemistry* 12: 3877-3882, 1973, but a lack of solubility and weak binding (large inhibitory constant) generally resulted.

Modifications to increase solubility soon established that the inhibitory properties of the peptides are markedly dependent on the hydrophobicity of various amino acid residues. These modifications also established that increasing solubility by replacing lipophilic amino acids with hydrophilic isosteric residues can become counter-productive. Other approaches to increasing solubility have also had limited success.

Modifications designed to increase binding to renin have also been made, but here too, with mixed results.

A series of inhibitors of renin have been disclosed which contain the unnatural amino acid, statine: see, e.g., Veber et al, U.S. Pat. Nos. 4,384,994 and 4,478,826; Evans et al, U.S. Pat. No. 4,397,786; Boger et al, *Nature*, 1983, 303, 81-84 and U.S. Pat. Nos. 4,470,971; 4,485,099; 4,663,310 and 4,668,770; Matsueda et al, EP-A 128 762, 152 255; Morisawa et al., EP-A 186 977; Riniker et al, EP-A 111 266; Bindra et al, EP-A 155 809; Stein et al, *Fed. Proc.* 1986, 45, 869; and Hölzemann et al, German Offenlegungsschrift DE 348545. Attempting to explain the effect of statine, Powers et al., in *Acid Proteases, Structure, Function and Biology*, Plenum Press, 1977, 141-157, observed that in pepstatin, statine occupies the space of the two amino acids on either side of the cleavage site of a pepsin substrate and Tang et al., in *Trends in Biochem. Sci.*, 1:205-208 (1976) and *J. Biol. Chem.*, 251: 7088-94, 1976, pointed out that the statine residue of pepstatin resembles the transition state for pepsin hydrolysis of peptide bonds.

Renin inhibitors containing other peptide bond isosteres, including a reduced carbonyl isostere have been disclosed by M. Szelke et al, in work described in published European Patent Applications 45 665 and 104 041; in U.S. Pat. No. 4,424,207, and in PCT Int. Appl. WO 84/03044; in *Nature*, 299, 555 (1982); *Hypertension*, 4, Supp. 2, 59, 1981; and British Patent 1,587,809. In *Peptides, Structure and Function: Proceedings of the Eighth American Peptide Symposium*, ed. V. J. Hruby and D. H. Rich, p. 579, Pierce Chemical Co., Rockford, Ill., 1983, Szelke et al also showed isosteric substitutions at the Leu-Leu site of cleavage, resulting in compounds with excellent potency.

Other peptide bond isosteres have then been disclosed in Buhlmayer et al in EP-A 144 290 and 184 550; Hester et al, EP-A 173 481; Raddatz, EP-A 161 588; Dann et al, *Biochem. Biophys. Res. Commun.* 1986, 134, 71-77; Fuhrer et al, EP-A 143 746; Kamijo et al, EP-A 181 110; Thaisrivongs et al, *J. Med. Chem.*, 1985, 28, 1553-1555; Ryono et al., EP-A 181 071; and Evans et al, U.S. Pat. No. 4,609,641.

Other modifications which have been tried include preparing renin inhibitors with non-peptide C-termini, such as disclosed in European Published Applications 172 346 and 172 347; Evans et al, *J. Med. Chem.*, 1985, 28, 1755-1756; Bock et al, *Peptides, Structure and Function: Proceedings of the Ninth American Peptide Symposium*, ed. C. M. Deber et al, pp. 751-754, Pierce Chemical Co., Rockford, Ill., 1985; and Plattner et al, in *Abstracts from the 191st National Meeting of the American Chemical Society*, April, 1986. Kokubu et al, in *Hypertension*, 1985, 7, Suppl. I, p. 8-10 and Matsueda et al, in *Chemistry Letters*, 1985, 1041-1044 and in European Published Applications 128 762 and 152 255 disclosed peptide aldehyde renin inhibitors, and Hanson et al in *Biochem. Biophys. Res. Commun.* 1985, 132, 155-161, reported peptide glycol inhibitors.

These various renin inhibitors all generally comprise peptide-based inhibitors in which a sequence of the type: ... A-B-D-E-F-G-J-K-L ..., where G is a peptide bond mimic and A,B,D,E,F,J,K, and L may individually be absent or may represent naturally-occuring or modified amino acids. Typical sequences of this type include:

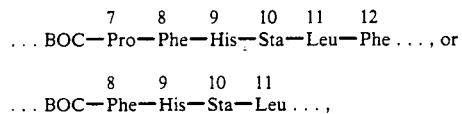

where the N-terminus typically comprises an amino acid protecting group such as BOC or CBZ, and the N-terminal amino acids are Pro-Phe-His or Phe-His.

Lower molecular weight renin-inhibitory di- or tripeptides comprising acyclic 2-substituted-4-amino-5-cyclohexyl-3-hydroxy-pentanoic acid (ACHPA) have been disclosed in U.S. patent application Ser. No. 045,941, filed May 4, 1987, and other lower molecular weight peptides have been disclosed in Sham, EP 184 855, Bindra et al, EP 155 809, and Matsueda et al, EP 152 255.

It is an object of this invention to prepare peptides which have enhanced oral activity as well as biological potency in inhibiting the renin enzyme. It is also an object to prepare peptides having a novel N-terminus in which the usual linkage which characterizes the bonding of amino acid to each other to form peptides is absent. It is an additional object of this invention to prepare peptides which have greater oral bioavailability and increased duration of action. It is still a further object of this invention to prepare novel peptides which are more useful antihypertensive agents, and compounds useful in treating hyperaldosteronism and congestive heart failure.

DETAILED DESCRIPTION OF THE INVENTION

The present invention is directed to renin-inhibitory di-, tri-, and tetrapeptides of the structure:

A-B-E-G-T-J wherein:

A is Het, where Het is a saturated or unsaturated 5 to 7-membered monocyclic or 7 to 10-membered bicyclic ring, which contains at least one and up to two nitrogen atoms (optionally quaternized or in the N-oxide form), may optionally be benzofused, and optionally may contain one additional ring atom chosen from among the list consisting of O, S, SO, and $SO_2$, and may optionally be substituted with one or two substituents independently selected from the group consisting of OH, $C_1$-$C_4$-alkyl, —$CF_3$, —CN, $C_1$-$C_4$-alkoxy, halo, aryl, where aryl is unsubstituted or mono-, di-, or trisubstituted phenyl or naphthyl, wherein the substituent(s) is-/are independently selected from the group consisting of $C_1$-$C_4$-alkyl, amino mono- or di-$C_1$-$C_4$-alkylamino, amino-$C_1$-$C_4$-alkyl, —OH, $C_1$-$C_4$-alkoxy, —$CF_3$, halo, —$CO_2H$, -$CO_2$-$C_1$-$C_4$-alkyl; -$NH_2$, mono- or di-$C_1$-$C_4$-alkylamino, —$CO_2H$, -$CO_2$-$C_1$-$C_4$-alkyl, —$SO_3H$, mono- or disubstituted $C_1$-$C_4$-alkyl, where the substituents(s) is/are independently selected from the group consisting of —$CO_2H$, -$CO_2$-$C_1$-$C_5$-alkyl; $C_1$-$C_5$-alkyl-CONH-, —OH, —$SO_3H$, $C_1$-$C_4$-alkyl-$SO_2$-, $C_1$-$C_4$-alkyl-SO-, -$SO_2NHCO$-$C_1$-$C_4$-alkyl, $C_1$-$C_5$-alkyl-OCONH-;

and where

N is present as a heteroatom in the heterocycle, the substituent may be —$(CH_2)_q$— or $(CH_2)_q$— or —$(CH_2)_2O(CH_2)_2$— where this substituent forms a quatenary spirocyclic ring with the N atom wherein q is 3 to 6. When the heterocyclic ring is quaternized, the counter-ion X- is chosen from the group consisting of chloride, bromide, iodide, or other monovalent anions such as acetate propionate, bisulfate, trifluoroacetate, benzoate, or maleate, succinate or tartrate. Alternatively, the heterocyclic ring may be substituted both with a substituent chosen from among those listed above and also with up to four $C_1$-$C_2$-alkyl, substituents, as for example where A is 3,3,5,5-tetramethyl-1-benzylpiperidin-4-yl;

Het $CH_2$— where Het is as defined above;

B is

r is 0-to-2, $A^1$ is hydrogen or $C_1$-$C_4$-alkyl.

$R_3$ is hydrogen, $C_1$-$C_4$-alkyl, $C_3$-$C_7$-cycloalkyl, aryl, as defined above, E is absent or is

$A^2$ is hydrogen or $C_1$-$C_4$-alkyl, r' is 1 to 4, $R^4$ is hydrogen, aryl, as defined above; $C_1$-$C_4$—OH; -$S(O)_r$-$C_1$-$C_4$-alkyl where r is as defined above, imidazol-4-yl, imidazol-2-yl, thiazol-5-yl, thiazol-4-yl.

G is

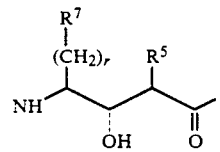

in which $R^5$ is hydrogen; $C_1$-$C_8$-alkyl, $C_2$-$C_8$-alkenyl; mono- or disubstituted $C_2$-$C_8$-alkyl, wherein the substituent(s) is/are independently selected from the group consisting of —OH, aryl, as defined above; unsubstituted ·or mono- or disubstituted $C_3$-$C_7$-cycloalkyl, wherein the substituents(s) is/are independently selected from the group consisting of $C_1$-$C_4$-alkyl, —$CF_3$, —OH, $C_1$-$C_4$-alkoxy and halo.

$R^7$ is $C_3$–$C_6$-alkyl; aryl, as defined above; or unsubstituted, mono- or disubstituted $C_3$–$C_7$-cycloalkyl, wherein the substituent(s) are

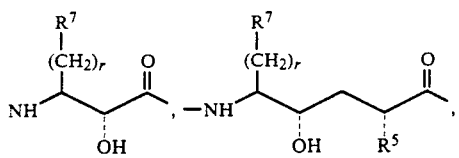

independently selected from the group consisting of $C_1$–$C_4$-alkyl, —$CF_3$, —OH, $C_1$–$C_4$-alkoxy, halo, or

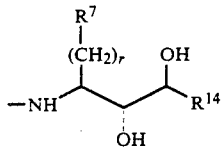

$R^{14}$ is hydrogen, unsubstituted or monosubstituted $C_1$–$C_6$-alkyl, where the substituent is amino or hydroxy, mono- or di-$C_1$–$C_4$-alkylamino, guanidino, $N(C_1$–$C_4$-alkyl$)_3{}^+A^-$ is as defined above, aryl-$C_1$–$C_4$-alkyl, where aryl is as defined above, $C_5$–$C_7$-cycloalkyl, [In this Case T and J are absent] and r, $R^7$ are as defined above;

T is absent or is

—NHCH[(CH$_2$)$_r$]R$^9$CO— r is as defined above;
$R^9$ is hydrogen $C_1$–$C_4$-alkyl, and
J is

—Y-(CH$_2$)$_x$[CH(R$_5$)]$_y$—(CH$_2$)$_z$—R$^{10}$

Y is O, NH, or N-$C_1$–$C_4$-alkyl.
x is 0 to 1.
y is 0 to 1.
z is 0 to 4.
s is 0 to 2.
$R^5$ is as defined above.
$R^{10}$ is hydrogen; —OH; aryl as defined above; Het, as defined above; —$NH_2$; —$NR^{17}R^{18}R^{19}{}^+A^-$, where $R^{17}$ and $R^{19}$ are independently $C_1$–$C_4$-alkyl, $R^{18}$ is aryl, Het or $C_1$–$C_4$-alkyl substituted with a substituent chosen from the group consisting of aryl, Het, —OH, —$NH_2$, —NH-$C_1$–$C_4$-alkyl, -N($C_1$–$C_4$-alkyl)$_2$, —$CO_2H$, or aryl, in which aryl and $A^-$ are as defined above;

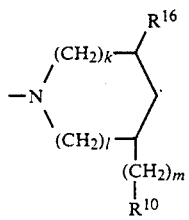

where k=1, 2; l=0, 1; $R^{16}$= —H, —OH, $C_1$–$C_4$-alkyl, aryl, or aryloxy wherein aryl is as defined; and $R^{10}$ is as defined above;

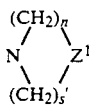

where k' and n=2 or 3; s'=1 or 2, $R^{10}$ is as defined above; and $Z^1$ is O, S, SO, $SO_2$, NH, $NR^{18}$ or $(NR^{17}R^{18})^+A^-$ where $R^{17}$, $R^{18}$ and $A^-$ are defined above;

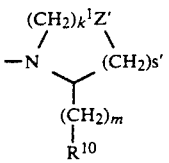

where K', s', $R^{10}$, and $Z^1$ are as defined above;

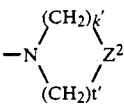

where t' is 2 or 3; k' is as defined above, and $Z^2$ is $NR^{18}$ or $N(R^{17}R^{18})^+A^-$, where $R^{17}$, $R^{18}$ and $A^-$ are as defined above;

or a pharmaceutically acceptable salt thereof.

In the peptides of the present invention, the components having asymmetric centers occur as racemates, racemic mixtures and as individual diastereomers, with all isomeric forms generally being included the present invention.

"Het" for example include piperidyl, piperidinyl, piperazinyl, 2-oxopiperazinyl, 2-oxopyrolodinal, 2-oxopiperidinyl, 2-oxoazepinyl, azepinyl, pyrryl, pyrrolinyl, 4-piperidonyl, pyrrolidinyl, pyrazolyl, pyrazolinyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, benzothiazolyl, benzoxazolyl, furyl, thienyl, benzothienyl, thiamorpholinyl, thiamorpholinyl sulfoxide, thiamorpholinyl sulfone and the like.

The abbreviations used herein have the following meaning:

| Abbreviated Designation | Amino Acid/Residue |
|---|---|
| ACHPA | (3S,4S)-4-amino-5-cyclohexyl-3-hydroxypentanoic acid |
| Ala | L-alanine |
| Arg | L-arginine |
| Cys | cysteine |
| Gly | L-glycine |
| His | D- or L-histidine |
| HomoPhe | homologated phenylalanine |
| HomoTrp | homologated tryptophan |
| HomoTyr | homologated tyrosine |
| Ile | L-isoleucine |
| Leu | L-leucine |
| Lys | L-lysine |
| Met | L-methionine |
| Nle | norleucine |
| Nva | norvaline |
| Orn | L-ornithine |
| (p-MeO)Phe | L-para-methoxyphenylalanine |
| Phe | L-phenylalanine |

| Abbreviated Designation | Amino Acid/Residue |
|---|---|
| Pro | L-proline |
| Sar | L-sarcosine (N-methylglycine) |
| Ser | L-serine |
| Sta | statine |
| Thr | L-threonine |
| Trp | L-tryptophan |
| Tyr | L-tyrosine |
| Val | L-valine |
| Nal | 3-(1-napthyl)-L-alanine |
| Thiz | 3-(thiazol-4-yl)-L-alanine |
| Protecting Group | |
| BOC | t-butyloxycarbonyl |
| CBZ | benzyloxycarbonyl(carbobenzoxy) |
| DNP | 2,4-dinitrophenyl |
| IPOC | isopropoxycarbonyl |
| Activating Group | |
| HBT(HOBt) | 1-hydroxybenzotriazole hydrate |
| HOSU | N-hydroxysuccinimide |
| Condensing Agent | |
| DCCI (DCC) | dicyclohexylcarbodiimide |
| DPPA | diphenylphosphorylazide |
| EDC | 1-(3-dimethylaminopropyl)-3-ethyl-carbodiimide hydrochloride |
| Reagent | |
| (BOC)$_2$O | di-t-butyl dicarbonate |
| DIBAL | diisobutylaluminum hydride |
| DIPEA | diisopropylethylamine |
| DMAP | 4-(dimethylamino)pyridine |
| TEA | triethylamine |
| TFA | trifluoroacetic acid |
| LAH | lithium aluminum hydride |
| LDA | lithium diisopropylamide |
| MCPBA | 3-chloroperoxybenzoic acid |
| Reagent | |
| NMM | N-methyl morpholine |
| PPTS | pyridinium para-toluenesulfonate |
| TBAF | tetra-n-butylammonium fluoride |
| Solvent | |
| HOAc (AcOH) | acetic acid |
| DMF | dimethylformamide |
| DMSO | dimethyl sulfoxide |
| EtOAc | ethyl acetate |
| EtOH | ethanol |
| Et$_2$O | ether |
| MeOH | methanol |
| THF | tetrahydrofuran |

Preferred compounds of the present invention include the following:

N-(2,2,6,6-Tetramethylpiperidin-4-yl)Phe-His-ACHPA-Ile-NHCH$_2$(pyridin-4-yl)

N-(N-Ethylpiperidin-3-yl)Phe-His-ACHPA-Ile-NHCH$_2$(pyridin-4-yl)

N-(N-Ethylpiperidin-4-yl)Phe-His-ACHPA-Ile-NHCH$_2$(pyridin-4-yl)

N-(N-Phenylpiperidin-3-yl)Phe-His-ACHPA-Ile-NHCH$_2$(pyridin-4-yl)

N-(N-Benzylpiperidin-3-yl)Phe-His-ACHPA-Ile-NHCH$_2$(pyridin-4-yl)

N-[(Pyridin-2-yl)methyl]Phe-His-ACHPA-Ile-NHCH$_2$(pyridin-4-yl)

N-[(Pyridin-4-yl)methyl]Phe-His-ACHPA-Ile-NHCH$_2$(pyridin-4-yl)

N-[(Pyridin-4-yl)methyl]Phe-His-ACHPA-Ile-NHCH$_2$(pyridin-4-yl)

[N-[(N-Methylpyridin-2-yl)methyl]Phe-His-ACHPA-Ile-NHCH$_2$-(pyridin-4-yl)]$^{30}$ Cl$^-$ N-[(Pyridin-2-yl)methyl]Phe-His-ACHPA-Ile-NHCH$_2$(pyridin-4-yl)

[N-(N-Methylpyridin-2-yl)Phe-His-ACHPA-Ile-NHCH$_2$-(pyridin-4-yl)]$^+$Cl$^-$

N-(Quinuclidin-3-yl)Phe-His-ACHPA-Ile-NHCH$_2$(pyridin-4-yl)

N-(Quinuclidin-4-yl)Phe-His-ACHPA-Ile-NHCH$_2$(pyridin-4-yl)

[N-(N-Methylquinuclidin-3-yl)Phe-His-ACHPA-Ile-NHCH$_2$(pyridin-4-yl)]$^+$Cl$^-$

[N-(N-Methylquinuclidin-4-yl)Phe-His-ACHPA-Ile-NHCH$_2$-(pyridin-4-yl)]$^+$Cl$^-$

[N-(N-(2-Hydroxy)ethylquinuclidin-4-yl)Phe-His-ACHPA-Ile-NHCH$_2$-(pyridin-4-yl)]$^+$Cl$^-$ N-(N-Carboxymethylquinuclidin-3-yl)Phe-His-ACHPA-Ile-NHCH$_2$-(pyridin-4-yl)]

[N-(N-Carboethoxymethylquinuclidin-3-yl)Phe-His-ACHPA-Ile-NHCH$_2$-(pyridin-4-yl)]$^+$Cl$^-$ N-Methyl-N-(quinuclidin-4-yl)Phe-His-ACHPA-Ile-NHCH$_2$-(pyridin-4-yl)

[N-(Methyl-N-(N-methylquinuclidin-4-yl)Phe-His-ACHPA-Ile-NHCH$_2$-(pyridin-4-yl)]$^+$Cl$^-$ N-Box-N-(quinuclidin-3-yl)Phe-His-ACHPA-Ile-NHCH$_2$(pyridin-4-yl)

N-(2-Benzylquinuclidin-3-yl)Phe-His-ACHPA-Ile-NHCH$_2$(pyridin-4-yl)

N-(Quinuclidin-3-yl)Phe-His-ACHPA-Ile-NHCH$_2$-(pyridin-4-yl)

N-(Quinuclidin-3-yl)Tyr(OMe)-His-ACHPA-Ile-NHCH$_2$(pyridin-4-yl)

N-(Quinuclidin-3-yl)HPhe-His-ACHPA-Ile-NHCH$_2$(pyridin-4-yl)

N-(Quinuclidin-3-yl)Phe-Nle-ACHPA-Ile-NHCH$_2$(pyridin-4-yl)

N-(Quinuclidin-3-yl)Phe-Thiz-ACHPA-Ile-NHCH$_2$(pyridin-4-yl)

N-(Quinuclidin-3-yl)Phe-Val-ACHPA-Ile-NHCH$_2$(pyridin-4-yl)

N-(Quinuclidin-3-yl)Phe-Phe-ACHPA-Ile-NHCH$_2$(pyridin-4-yl)

N-(Quinuclidin-3-yl)Tyr(OMe)-Nle-ACHPA-Ile-NHCH$_2$(pyridin-4-yl)

N-(Quinuclidin-3-yl)Nal-Nle-ACHPA-Ile-NHCH$_2$(pyridin-4-yl)

N-(Quinuclidin-3-yl)Phe-Nle-ACHPA-Leu-NHCH$_2$(pyridin-4-yl)

N-(Quinuclidin-3-yl)Phe-Nle-ACHPA-Phe-NHCH$_2$(pyridin-4-yl)

N-(Quinuclidin-3-yl)Phe-Nle-ACHPA-NHCH$_2$-(pyridin-4-yl)

N-(Quinuclidin-3-yl)Phe-Nle-ACHPA-NHCH$_2$-(pyridin-3-yl)

N-(Quinuclidin-3-yl)Phe-Nle-ACHPA-2(S)-methylbutyl

N-(Quinuclidin-3-yl)Phe-Nle-ACHPA-Ile-NHCH$_2$(pyridin-2-yl)

N-(Quinuclidin-3-yl)Phe-Nle-ACHPA-Leu-NHCH$_2$CH$_2$(imidazol-4-yl)

N-(Quinuclidin-3-yl)Phe-His-ACHPA-(N-methyl)Ile-NHCH$_2$(pyridin-4-yl)

N-(Quinuclidin-3-yl)Phe-His-ACHPA-Ile-NH-(quinuclidin-3-yl)

[N-(Quinuclidin-3-yl)Phe-His-ACHPA-Ile-NH-(N-methylquinuclidin-3-yl)]$^+$OAc$^-$ N-(Quinuclidin-3-yl)Phe-His-Cal[CH(OH)CH$_2$]Val-NHCH$_3$ N-(Quinuclidin-3-yl)Phe-His-Cal[CH(OH)CH$_2$]Ala-NHCH$_3$ N-(Quinuclidin-3-yl)Phe-(NCl-Me)His-Cal[CH(OH)CH$_2$]Ala-NHCH$_3$ N-(Quinuclidin-3-yl)Phe-(N-Me)Nle-Cal[CH(OH)CH$_2$]Ala-NHCH$_3$ N-(Quinuclidin-3-yl)Nal-(N-Me)Nle-Cal[CH(OH)CH₂]Ala-NHCH₃

N-(Quinuclidin-3-yl)Nal-(N-Me)Nle-Cal[CH(OH)CH₂]Ala-NHCH₂(pyridin-4-yl)

N-(Quinuclidin-3-yl)Phe-His-Cal[CH(OH)CH₂]Ala-NHCH₂(pyridin-4-yl)

N-(Quinuclidin-4-yl)Phe-His-Cal[CH(OH)CH₂]Ala-NH-CH₃

[N-(N-Methylquinuclidin-3-yl)Phe-His-Cal[CH(OH)CH₂]Ala-NHCH₃]+Cl−

[N-(N-Methylquinuclidin-4-yl)Phe-His-Cal[CH(OH)CH₂]Ala-NHCH₃]+Cl−

[N-(N-Benzylquiniuclidin-3-yl)Phe-His-Cal[CH(OH)CH₂]Ala-NHCH₃]+Cl−

N-(N-Carboxymethylquinuclidin-3-yl)Phe-His-Cal[CH(OH)CH₂]Ala-NHCH₃]

[N-(N-Carboethoxyxymethylquinuclidin-3-yl)Phe-His-Cal[CH(OH)CH₂]Ala-NHCH₃]+Cl−

N-Methyl-N-(quinuclidin-4-yl)Phe-His-Cal-[CH(OH)CH₂]Ala-NHCH₂(pyridin-4-yl)

N-Methyl-N-(N-methylquinuclidin-4-yl)Phe-His-Cal[CH(OH)CH₂]Ala-NHCH₃+Cl−

N-Boc-N-(quinuclidin-3-yl)Phe-His-Cal-[CH(OH)CH₂]Ala-NHCH₂(pyridin-4-yl)

N-(2-Benzylquinuclidin-3-yl)Phe-His-Cal[CH(OH)CH₂]Ala-NHCH₂(pyridin-4-yl)

N-(Quinuclidin-3-yl)Phe-His-ACHPA-N(CH₂CH₃)CH₂CH₂N(CH₂CH₃)₂

N-(Quinuclidin-3-yl)Phe-His-ACHPA-N(CH₂CH₃)CH₂CH₂N(CH₂CH₃)₂O

N-(Quinuclidin-3-yl)Phe-His-ACHPA-N(CH₂CH₃)CH(OH)CH₂N(CH₂CH₂)₂O

[N-(Quinuclidin-3-yl)Phe-His-ACHPA-(CH₂CH₃)CH₂CH(OH)CH₂N(CH₃)(CH₂CH₂)₂O]+Cl−

N-(Quinuclidin-3-yl)Phe-His-ACHPA-N(CH₂CH₃)CH₂(pyridin-4-yl)

N-(Quinuclidin-3-yl)Phe-His-ACHPA-N(CH₂CH₃)CH₂CH₂(pyridin-4-yl)

N-(Quinuclidin-3-yl)Phe-His-ACHPA-N(CH₂CH₂)₂O

N-(Quinuclidin-3-yl)Phe-His-ACHPA-N(CH₂CH₃)-2(S)-methylbutyl

N-(Quinuclidin-3-yl)Phe-His-ACHPA-N(CH₂CH₃)(CH₂)₃CH₃

N-(Quinuclidin-3-yl)Phe-His-ACHPA-N(CH₂CH₃)(2,2,6,6-tetramethylpiperidin-4-yl)

N-(Quinuclidin-3-yl)Phe-His-ACHPA-N[(CH₂)₄]CH₂CH(-)N-(CH₂CH₃)₂

N-(Quinuclidin-3-yl)Phe-His-ACHPA-NH(quinuclidin-3-yl)

[N-(Quinuclidin-3-yl)Phe-His-ACHPA-NH(N-methylquinuclidin-3-yl)]+OAc−

N-(Quinuclidin-3-yl)Phe-His-norACHPA-O-iPr

N-(Quinuclidin-3-yl)Phe-His-norACHPA-NH(CH₂)₂N(CH₂CH₂)₂O

N-(Quinuclidin-3-yl)Phe-His-norACHPA-O-2(S)-methylbutyl

[N-(N-Benzylquinuclidin-3-yl)Phe-His-norACHPA-O-2(S)-methylbutyl]+−OCOPh

N-(N-Carboxymethylquinuclidin-3-yl)Phe-His-norACHPA-O-iPr

N-(2,2,6,6-tetramethylpiperidin-4-yl)Phe-His-norACHPA-O-iPr

N-[N-(Quinuclidin-3-yl)Phe-His-]-2(S)-amino-1-cyclohexyl-3(S)-hydroxy-6-methylheptane N-[N-(Quinuclidin-3-yl)Phe-His-]-2(S)-amino-1-cyclohexyl-3(S), 4(R)-dihydroxy-6-methylheptane

[N-[N-(N-methylquinuclidin-3-yl)Phe-His-]-2(S)-amino-1-cyclohexyl-3(S), 4(R)-dihydroxy-6-methylheptane]+OAc−

N-[N-(Quinuclidin-3-yl)Phe-His-]-2(S)-amino-1-cyclohexyl-3(R), 4(S)-dihydroxy-5-methylheptane N-[N-(Quinuclidin-3-yl)Phe-His-]-4(S)-amino-1-cyclohexylmethyl-2(S), 3(R)-dihydroxy-1-(isopropylsulfonyl)pentane

[N-(N-Benzylquinuclidin-3-yl)Phe-ACHPA-Ile-NHCH₂(pyridin-4-yl)]+OAc−

N-(N-Benzylquinuclidin-3-yl)Phe-ACHPA-Ile-NHCH₂(pyridin-4-yl)

[N-(N-Methyl-2-benzylquinuclidin-3-yl)Phe-ACHPA-Ile-NHCH₂(pyridin-4-yl)]+OAc−

[N-(2-benzylquinuclidin-3-yl)His-ACHPA-Ile-NHCH₂(pyridin-4-yl)]

[N-(2-benzylquinuclidin-3-yl)Nle-ACHPA-Ile-NHCH₂(pyridin-4-yl)]

[N-(N-Benzylquinuclidin-3-yl)Nle-ACHPA-Ile-NHCH₂(pyridin-4-yl)]+OAc−

N-(2-Benzylquinuclidin-3-yl)His-Cal[CH(OH)CH₂]Ala-NHCH₂(pyridin-4-yl)

N-(2-Benzylquinuclidin-3-yl)His-Cal[CH(OH)CH₂]Ala-NHCH₃

N-(2-Benzylquinuclidin-3-yl)Nle-Cal[CH(OH)CH₂]Ala-NHCH₃

[N-(N-Methyl-2-benzylquinuclidin-3-yl)His-Cal[CH(OH)CH₂]Ala-NHCH₂(pyridin-4-yl)]+OAc−

Peptide renin inhibitors of Formula I may be prepared in accordance with well-known procedures for preparing peptides from their constitutent amino acids.

Structures and abbreviations for the G components of the renin-inhibitory peptides of the present invention are shown below:

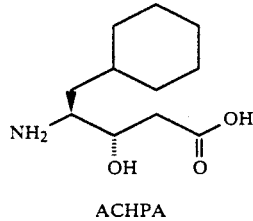

ACHPA

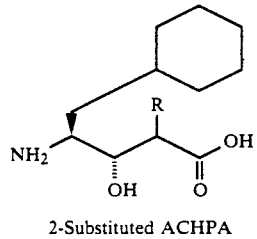

2-Substituted ACHPA

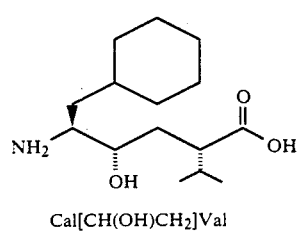

Cal[CH(OH)CH₂]Val

-continued

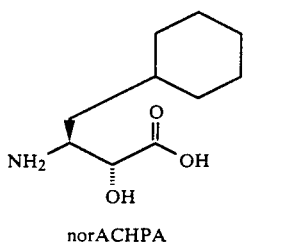

norACHPA

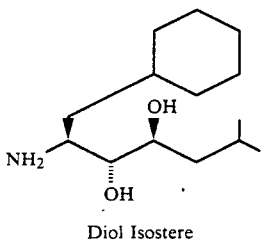

Diol Isostere

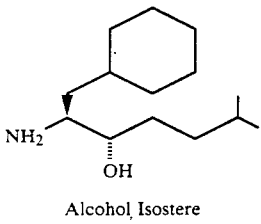

Alcohol Isostere

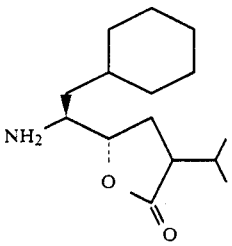

Cal[CH(OH)CH$_2$]Val lactone

The G components indicated above may be prepared by the following methods:
1. Boc-ACHPA-OEt may be prepared by the method described by Boger et al., *J. Med. Chem.* 1985, 28, 1779-1790 or that described by Schuda et al., *J. Org. Chem.*, 1988, 53, 873-875.
2. Boc-Cal[CH(OH)CH$_2$]Val-OH δ-lactone may be obtained from intermediates prepared using methods described by P. Buhlmayer et al. in European Patent Application 0,184,550-A2. Synthetic routes to similar peptide bond isosteres are described in the following:
   a. Szelke et al., in *Peptides, Structure and Function, Proceedings of the Eighth American Peptide Symposium* (ed. V. J. Hrudy and D. H. Rich) pp. 579-82. Pierce Chemical Co., Rockford, Ill.
   b. D. T. Pals et al in European Patent Application 0,173,481-A2.
   c. B. E. Evans et al., *J. Org. Chem.*, 50, 4615-1625 (1985).
   d. A. H. Fray et al., *J. Org. Chem.*, 51 4828-4833 (1986).
   e. M. Szelke et al., PCT Int. Appl. WO 84 03,044.
   f. D. J. Kempf, *J. Org. Chem.*, 51, 3921-3926 (1986).

3. Efficient methods for preparing the 2-substituted ACHPA component G in a suitably protected form are described in Merck U.S. Pat. No. 4,663,310. Other pertinent references are D. Veber et al., *Biochem. Soc. Trans.*, 12, 956-959 (1984).
4. Methods for preparing the alcohol and diol isosteres illustrated above, and related analogs, are described in the following references:
   a. J. R. Luly et al., *J. Org. Chem.*, 52, 1487-1492 (1987).
   b. S. H. Rosenberg et al., *J. Med. Chem.*, 30, 1224-1228 (1987).
   c. J. R. Luly et al., *J. Med. Chem.*, 30, 1609-1616 (1987).
   d. G. Bolis et al., *J. Med. Chem.*, 30, 1729-1737 (1987).
   e. J. R. Luly et al., *Biochem. Biophys. Res. Commun.*, 143, 44-51 (1987).
   f. J. R. Luly et al., *J. Med. Chem.*, 31, 532-539 (1988).
5. A Method for preparing norACHPA may be found in Iizuka et al., European Patent Application No. 0,244,083 (1987).

The peptide coupling reactions referred to below in Routes A, B and C include those brought about by the action of DCC/HOBt (dicyclohexylcarbodiimide/N-hydroxybenzotriazole), DPPA (diphenylphorylazide), "BOP reagent" (benzotriazol-1-yloxytris(dimethylamino)phosphonium hexafluorophosphate), BOP-Cl (bis(2-oxo-3-oxazolidinyl)phosphinic chloride), DSS (N,N'-disuccinimidyl oxalate), and other well-known coupling reagents.

N-alkylated amino acids, referred to below as A(A$^1$)N-AA$^1$ or A(A$^1$)N-AA$^2$, represent mono- or dialkylated amino acids. These are prepared by standard reductive alkylation procedures, such as those brought about by the action of sodium cyanoborohydride or sodium borohydride. The carbonyl components used include aldehydes and ketones. Often an excess of the carbonyl component is used. The carbonyl component may contain additional functional groups, which are usually protected with protecting groups. For example, carboxylic esters are esterified and amino groups are protected as Cbz derivatives. The carbonyl component may alternatively contain a quaternized amine group. When mono N-alkylated amino acids are used in coupling reactions, the basic secondary amine function may be protected as a Boc derivative or may be left unprotected during the coupling reaction, which is usually brought about by the action of DCC and HOBt.

The R$^{2c}$R$^{2d}$NH components referred to in the synthetic routes described below are in general taken to represent the J component of Formula I. It is understood that when a T component is present in an inhibitor of Formula I, that this inhibitor may be prepared by replacing R$^{2c}$R$^{2d}$NH in the routes described below by a component represented by AA$^3$-NR$^{2c}$R$^{2d}$. In such a case the side-chain of AA$^3$ may require the presence of a protecting group during the coupling steps described; protecting groups used are those described below as used for the protection of the side-chains of amino acids AA$^1$ and AA$^2$.

Peptides of Formula I which contain ACHPA are prepared using the following procedures:

ROUTE A

Step A1

Boc-ACHPA-OEt is treated with anhydrous TFA to remove the Boc protecting group, giving ACHPA-OEt.

Step A2

Using standard methods, a dipeptide protected at the N-terminus with a Boc group (Boc-AA$^2$-AA$^1$) is coupled to ACHPA-OEt, giving a coupled product 3. Alternatively, Boc-AA$^1$ is coupled to ACHPA-OEt giving 1. The coupled product 1 is treated with anhydrous TFA to removed the Boc protecting group, and the resulting product 2 is coupled with Boc-AA$^2$, giving 3.

Step A3

The resulting coupled product 3 is treated with methanolic hydrazine, giving the corresponding hydrazide 4.

Step A4

Hydrazide 4 is treated with acidic isoamyl nitrite, producing the corresponding acyl azide, which is treated in situ with an amine $R^{2c}R^{2d}NH$, giving coupled product 5. Alternatively, coupled product 3 is treated with sodium hydroxide in THF-H$_2$O and the resulting carboxylic acid derivative coupled with $R^{2c}R^{2d}NH$, giving 5. Additional reactive functional groups in the amino component $R^{2c}R^{2d}NH$ are protected with protecting groups, such as Cbz for amino groups, benzyl ethers for alcohols, and benzyl esters for carboxylic acids.

Step A5

The N-terminal Boc protecting group is then removed from 5 by treatment with anhydrous TFA, and the resulting tripeptide analog 6 treated with a carbonyl component (for example, a ketone or aldehyde or ketoester) and sodium cyanoborohydride, giving the alkylated tripeptide derivative 7.

Step A5a

Alternatively, compound 7 may be prepared using the following sequence: Ester 1 is treated with anhydrous hydrazine, giving hydrazide 4a. This hydrazide is treated with acidic isoamyl nitrite and then with $R^{2c}R^{2d}NH$ and base, to give the coupled product 5a. Treatment of 5a with anhydrous TFA then affords the tripeptide amide 6a. Coupling of 6a to an N-alkylated amino acid A(A$^1$)N-AA$^2$ then provides 7.

Step A6

During the steps above, reactive functional groups present in the side-chains of amino acid components or in the $R^{2c}R^{2d}NH$-element are protected with protecting groups. These may be Cbz groups for amines, benzyl ethers for 175 alcohols, and benzyl esters for carboxylic acids. In the case of histidine, the Boc protecting may be used for protection of the side-chain imidazole ring; this group is removed in step 3 (or step 5a) during the treatment with hydrazine. Thereafter the histidine imidazole ring may be left unprotected.

Step A7

Protecting groups are removed from 7 by hydrogenolysis, giving 8.

Step A8

In cases where a quaternized amino group is to be introduced into the C-terminal $R^{2c}R^{2d}NH$-element of compound 8, one of the following procedures is followed t introduce the quaternized amine group:

PROCEDURE 1

A tertiary amine within the R$_1$ or R$_2$ group of $R^{2c}R^{2d}NH$ is quaternized by treatment of $R^{2c}R^{2d}NH$-Boc with an alkyl halide and KHCO$_3$ in methanol or ethanol, or with an alkyl halide in DMF. The resulting quaternary ammonium salt is then treated with anhydrous TFA to remove the Boc protecting group, and the resulting amine used in coupling step A4 or A5a above.

PROCEDURE 2

A compound 7, in which the $R^{2c}R^{2d}NH$-element contains a tertiary amine, is prepared according to steps A1 to A6, and then the tertiary amine is then quaternized by treatment with an alkyl halide in DMF. In this latter case, histidine, when present as the AA$^1$ element, must first be reprotected as the Boc derivative by treatment of 7 with di-t-butyldicarbonate. The Boc group is then removed after step A7 by treatment of 8 with K$_2$CO$_3$ in methanol or with anhydrous ammonia in DMF or methanol.

| Compound | Formula |
|---|---|
| 1 | Boc—AA$^1$—ACHPA—OEt |
| 2 | AA$^1$—ACHPA—OEt |
| 3 | Boc—AA$^2$—AA$^1$—ACHPA—OEt |
| 4 | Boc—AA$^2$—AA$^1$—ACHPA—NHNH$_2$ |
| 4a | Boc—AA$^1$—ACHPA—NHNH$_2$ |
| 5 | Boc—AA$^2$—AA$^1$—ACHPA—NR$^{2c}$R$^{2d}$ |
| 5a | Boc—AA$^1$—ACHPA—NR$^{2c}$R$^{2d}$ |
| 6 | AA$^2$—AA$^1$—ACHPA—NR$^{2c}$R$^{2d}$ |
| 6a | AA$^1$—ACHPA—NR$^{2c}$R$^{2d}$ |
| 7,8 | A(A$^1$)N—AA$^2$—AA$^1$—ACHPA—NR$^{2c}$R$^{2d}$ |

ROUTE B

Step B1

Boc-ACHPA-OEt is treated with sodium hydroxide in THF-H$_2$O, giving Boc-ACHPA.

Step B2

Boc-ACHPA is coupled with an amine component $R^{2c}R^{2d}NH$, giving coupled product 9.

Step B3

Compound 9 is treated with anhydrous TFA to remove the Boc protecting group, giving 10.

Step B4

Compound 10 is coupled with a dipeptide protected at the N-terminus with a Boc protecting group (Boc-AA$^2$-AA$^1$), giving coupled product 12. Alternatively, 10 is coupled with Boc-AA$^1$, giving 11. Treatment of 11 with anhydrous TFA and coupling of the resulting product with Boc-AA$^2$ gives 12.

Step B5

The N-terminal Boc protecting group is then removed from 12 by treatment with anhydrous TFA, and the resulting tripeptide analog 13 treated with a carbonyl component and sodium cyanoborohydride as described in step A5. This gives alkylated tripeptide derivative 7. Alternatively, 11 may be treated with anhydrous TFA and the resulting amine coupled to an N-alkylated amino acid $A(A^1)N-AA^2$, providing 7.

Step B6

As described above in route A, reactive functional groups in amino acid side chains of $AA^1$ and $AA^2$, in the $R^{2c}R^{2d}N$- and A components are protected during the coupling steps above. The protecting groups are now removed from coupled product 7 by hydrogenolysis giving compound 8.

Step B7

In cases where a quaternized amino group is to be introduced into the C-terminal $R^{2c}R^{2d}N$-element of compound 8, one of the following procedures is followed to introduce the quaternized amine group:

PROCEDURE 1

A tertiary amine within the $R_1$ or $R_2$ group of $R^{2c}R^{2d}NH$ is quaternized by treatment of $R^{2c}R^{2d}N$-Boc with an alkyl halide and $KHCO_3$ is methanol or ethanol, or with an alkyl halide in DMF. The resulting quaternary ammonium salt is then treated with anhydrous TFA to remove the Boc protecting group, and the resulting amine used in coupling step 3 above.

PROCEDURE 2

A compound 7, in which the $R^{2c}R^{2d}N$-element contains a tertiary amine, is prepared according to steps B1 to B5, and the tertiary amine is then quaternized by treatment with an alkyl halide in DMF. In this latter case, histidine, when present as the $AA^2$ element, must first be reprotected as the Boc derivative by treatment of 7 with di-t-butyldicarbonate. The BOC group is then removed after step B6 by treatment of 8 with $K_2CO_3$ in methanol or with anhydrous ammonia in DMF or methanol.

| Compound | Formula |
|---|---|
| 9  | Boc—ACHPA—NR$^{2c}$R$^{2d}$ |
| 10 | ACHPA—NR$^{2c}$R$^{2d}$ |
| 11 | Boc—AA$^1$—ACHPA—NR$^{2c}$R$^{2d}$ |
| 12 | Boc—AA$^2$—AA$^1$—ACHPA—NR$^{2c}$R$^{2d}$ |
| 13 | AA$^2$—AA$^1$—ACHPA—NR$^{2c}$R$^{2d}$ |

Peptides of Formula I which contain a 2-substituted ACHPA element as a peptide bond mimic may be prepared as described above in Routes A and B except that Boc-ACHPA-OEt is replaced with a suitably protected 2-substituted ACHPA for example Boc-(2-allyl)ACHPA-OEt. In this way, peptides such as 16 may be prepared.

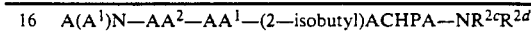
| 16 | A(A$^1$)N—AA$^2$—AA$^1$—(2—isobutyl)ACHPA—NR$^{2c}$R$^{2d}$ |

Peptides of Formula I which contain Cal[CH(OH)CH$_2$]Val as a peptide bond mimic are prepared as described below in Route C.

ROUTE C

Step C1

Lactone 17 is treated with potassium hydroxide to give the corresponding hydroxyacid 18. The hydroxyacid 18 is treated with t-butyldimethylsilyl chloride and imidazole, then with HOAc in THF-H$_2$O, giving the protected hydroxyacid 19.

| 17 | Boc—Cal[CH(OH)CH$_2$]Val lactone |
| 18 | Boc—Cal[CH(OH)CH$_2$]Val—OH |
| 19 | Boc—Cal[CH(OTBDMS)CH$_2$]Val—OH |

Step C2

Protected hydroxyacid 19 is coupled with an amino component $R^{2c}R^{2d}NH$, giving 20. Additional reactive functional groups in the amino component $R^{2c}R^{2d}NH$ are protected with protecting groups such as Cbz for amino and guanidino groups, benzyl ethers for alcohols, and benzyl esters for carboxylic acids.

Step C3

The Boc protecting group is removed from 20 by treatment with anhydrous TFA, giving 21.

| 20 | Boc—Cal[CH(OTBDMS)CH$_2$]Val—NR$^{2c}$R$^{2d}$ |
| 21 | Cal[CH(OTBDMS)CH$_2$]Val—NR$^{2c}$R$^{2d}$ |

Step C4

Compound 21 is coupled with a Boc-protected amino acid (Boc-AA$^1$) or a dipeptide with an N-terminal Boc protecting group (Boc-AA$^2$-AA$^1$), giving coupled product 22 or 23.

| 22 | Boc—AA$^1$—Cal[CH(OTBDMS)CH$_2$]Val—NR$^{2c}$R$^{2d}$ |
| 23 | Boc—AA$^2$—AA$^2$Cal[CH(OTBDMS)CH$_2$]Val—NR$^{2c}$R$^{2d}$ |

Step C5

The N-terminal Boc protecting group of 22 or 23 is removed by treatment with anhydrous TFA in CH$_2$Cl$_2$, giving 24 or 25.

| 24 | AA$^1$—Cal[CH(OTBDMS)CH$_2$]Val—NR$^{2c}$R$^{2d}$ |
| 25 | AA$^2$—AA$^1$—Cal[CH(OTBDMS)CH$_2$]Val—NR$^{2c}$R$^{2d}$ |

Step C6

Compound 24 or 25 is treated with a carbonyl component (an aldehyde, ketone or ketoester) and sodium cyanoborohydride, affording alkylated, ketone or ketoester) and sodium cyanoborohydride, affording alkylated tripeptide derivative 26 or 27. Additional reactive functional groups within the alkylated amino acid $A(A^1)N-AA^2$ are protected with protecting groups as described above.

| 26 | A(A$^1$)N—AA$^1$—Cal[CH(OTBDMS)CH$_2$]Val—NR$^{2c}$R$^{2d}$ |
| 27 | A(A$^1$)N—AA$^2$—AA$^1$—Cal[CH(OTBDMS)CH$_2$]Val—NR$^{2c}$R$^{2d}$ |

Step C7

The silyl protecting group is removed from 26 or 27 by treatment with fluoride. Other protecting groups are then removed by hydrogenolysis, giving 28 or 29.

| 28 | A(A$^1$)N—AA$^1$—Cal[CH(OH)CH$_2$]Val—NR$^{2c}$R$^{2d}$ |

| | |
|---|---|
| 29 | A(A$^1$)N—AA$^2$—AA$^1$—Cal[CH(OH)CH$_2$]Val—NR$^{2c}$R$^{2d}$ |

Step C8

In some cases a quaternized amino group is present in the C-terminal R$^{2c}$R$^{2d}$N-element of compound 26 or 27. In this case, a tertiary amine within R$^{2c}$ or R$^{2d}$ of R$^{2c}$R$^{2d}$NH is quaternized by treatment of R$^{2c}$R$^{2d}$N-BOC with an alkyl halide and KHCO$_3$ in methanol or ethanol or with an alkyl halide in DMF. The resulting quaternary ammonium salt is then treated with anhydrous TFA to remove the BOC protecting group, and the resulting amine used in coupling step C2 above. Alternatively, a compound 26 or 27 containing a tertiary amine in the R$^{2c}$R$^{2d}$N-element may be prepared as described above in steps C1 to C6. Then the silyl protecting group is removed from 26 or 27 by treatment with fluoride. If histidine is present as the AA$^1$ component, the imidazole ring is protected next by treatment with di-t-butyldicarbonate and Et$_3$N in methanol or DMF. The tertiary amine present in the R$^{2c}$R$^{2d}$N-element is then quaternized by treatment with an alkyl halide in DMF. Protecting groups present in the molecule are then removed by hydrogenolysis, as described in step C7, giving 28 or 29.

Step C9

It is understood that during the steps above, the reactive functional groups in the side-chains of amino acid components are protected with protecting groups, which are removed in the above hydrogenolysis step. These protecting groups may be Cbz for amines and guanidines, and benzyl ethers for alcohols. If histidine is present as AA$^1$, the side-chain imidazole ring is protected with a Boc group which is removed by TFA in step C3. Thereafter the side-chain of histidine is left unprotected. Alternatively, histidine with a DNP protecting group may be used. In this case, the DNP group is removed after step C7 by treatment of 28 or 29 with thiophenol. In cases where the T and J elements of inhibitors of Formula I are absent, the C-terminal G element is prepared as described in the references listed above and is, in general, coupled as described above for Boc-ACHPA-OEt to give, for example, the following:

| | |
|---|---|
| 30 | A(A$^1$)N—AA$^2$—AA$^1$—norACHPA—O—iPr |
| 31 | A(A$^1$)N—AA$^2$—AA$^1$—NHCH(CH$_2$—cyclohexyl)CH(OH)—CH$_2$(CH$_3$)$_2$ |
| 32 | A(A$^1$)N—AA$^2$—AA$^1$—NHCH(CH$_2$—cyclohexyl)CH(OH)CH—(OH)CH$_2$CH(CH$_3$)$_2$ |

Renin-inhibitors potencies were determined against human plasma renin and are expressed as IC$_{50}$ values.

EXAMPLE 1

N$^\alpha$-(Quinuclidin-3(RS)-yl)-phenylalanine-t-butyl ester hydrochloride

To a solution of 0.09 g (56.25 mmol) 3-quinuclidinone and 4.15 g (18.75 mmol) Phe-O-t-Bu in 50 ml methanol was added over a 12 hour period a solution of 2.95 g (46.9 mmol) sodium cyanoborohydride in 13 ml methanol. After stirring for an additional 8 hours, 5.78 g (50.0 mmol) pyridine hydrochloride was added and after 1½ hours stirring, sodium chloride was removed by filtration. The filtrate was concentrated to a foam which was treated with 15 ml methanol and 50 ml ethyl acetate to give a slurry of the byproduct 3-hydroxy quinuclidine hydrochloride (74% of excess) which was removed by filtration. The filtrate was concentrate to an oil and charged with 10 ml methanol to a 5×200 cm column of LH-20 and eluted with methanol. The product fraction contained 6.54 g of a mixture of diastereomers in a 55:45 ratio as established by HPLC.

EXAMPLE 2A

N$^\alpha$-(Quinuclidin-3(S)-yl)-phenylalanine-t-butyl ester hydrochloride

A solution of 7.0 g of the isomer mixture (from Example 1) in 25 ml water was treated with 2.62 g sodium bicarbonate bringing the pH to 9.0. The clear solution was lyophilized and the crystalline residue was extracted with 50 ml of acetonitrile. Evaporation of the solvent and treatment with 25 ml ether gave crystals which were filtered off, washed with ether, and dried. The yield was 2.49 g (65%) of an isomer established by x-ray crystal structure analysis to be the S,S-diastereomer hydrochloride.

EXAMPLE 2B

N$^\alpha$-(3S)-Quinuclidinyl)-Phe-O-t-Bu.HCl

A solution of 13.6 g of the isomeric mixture (Example 1) in 10 ml methanol was triturated with 50 ml ethyl ether and the crystals were collected by filtration, washed and dried to yield 4.76 g (64%) of the major isomer, as the dihydrochloride. HPLC showed a single component.

EXAMPLE 3

N$^\alpha$-(Quinuclidin-3(S)-yl)Phe-O-t-Bu.2HCl

A solution of 1.91 g of the tertiary butyl ester (from Example 2A) in 3 ml concentrated hydrochloric acid was left for 3 hours and then concentrated to an amorphous mass. To remove excess HCl the material was redissolved in 10 ml water and concentrated to yield 1.98 g of the dihydrochloride.

EXAMPLE 4

[N$^\alpha$-(N-Methylquinuclidin-3(S)-yl)Phe-O-t-Bu]+I$^-$

A solution of 406 mg (1.23 mM) of the product of Example 2A in 2 ml methanol was treated with 310 μl. (5.0 mmol) methyl iodide and 68.3 mg (1.26 mmol) sodium methylate. After 2 hours at room temperature the reaction mixture was concentrated and charged with 4 ml of methanol to a 2.5×210 cm column of LH-20 and eluted with methanol. The product fractions contained 366 mg of product with an NMR spectrum consistent with the assigned structure.

EXAMPLE 5

N$^\alpha$-(N-Methylquinuclidin-3(S)-yl)-phenylalanine]+Cl$^-$.HCl

A solution of 366 mg (775 μM) of the t-Butyl ester (Example 2A) in 1 ml of water and 2 ml of conc. hydrochloric acid was aged for 2 hours, concentrated and charged with 2 ml methanol to 2.5×210 cm LH20 column and eluted with methanol. The product fraction contained 254 mg of product with NMR and mass spectra consistent with the structure.

EXAMPLE 6

$N^\alpha$-(1-Benzylpiperidin-4-yl)Phe-O-t-Bu

A solution of 11.36 g (60.0 mM) 1-Benzyl-piperidin-4-one and 4.43 g (20.0 mmol) Phe-O-t-Bu and 3.6 ml (60 mmol) of acetic acid in 40 ml of methanol was treated over a 10 hour period with a solution of 3.15 gm (50.0 mmol) sodium cyanoborohydride in 8 ml methanol. After stirring for 57 hours, 15.03 g (130 mM) pyridine hydrochloride was added and after stirring for 2 hours sodium chloride was removed by filtration. The solvent was removed and the amorphous residue was treated with 50 ml of ethyl acetate giving a crystalline mass. After filtration and washing with 50 ml of acetonitrile there was obtained 4.59 g (49.0%) of product. NMR and mass spectra were in accord with the assigned structure.

EXAMPLE 7

$N^\alpha$-(2,2,6,6-Tetramethylpiperidin-4-yl)-Phe-O-t-Bu

A solution of 11.55 g (60.2 mmol) 2,2,6,6-tetramethyl-piperidin-4-one hydrochloride and 4.44 g (20 mmol) Phe-O-t-Bu in 40 ml of methanol was treated over an eight hour period with a solution of 3.19 g (50.8 mmol) sodium cyanoborohydride in 6 ml of methanol. After stirring overnight a solution of 8.21 g (71.0 mmol) pyridine hydrochloride in 20 ml of methanol was added and stirring continued for 1½ hour. Sodium chloride was removed by filtration, and the filtrate was concentrated to an oil. The byproduct 2,2,6,6-tetramethylpiperidin-3-ol (69.5% of excess) crystallized on addition of 40 ml ethyl acetate and 40 ml of acetonitrile, and was removed by filtration. The filtrate was concentrated to an amorphorus mass which was charged with 10 ml methanol to a 5×200 cm LH-20 column and eluted with methanol. Evaporation of the solvent from the product-containing fractions and crystallization from 10 ml acetonitrile afforded 5.34 g (61.5%) of product, which had NMR and mass spectra in accord with assigned structure.

EXAMPLE 8

$N^\alpha$-(1-Ethylpiperidin-3(RS)-yl)]Phe-O-t-Bu

A solution of 8.18 g (50.0 mmol) 1-ethyl-3-piperidone HCl, 5.15 g (20.0 mM) Phe-O-t-Bu and 1.64 g (19.3 mM) sodium acetate in 250 ml methanol was treated over a 14 hour period with a solution of 1.88 g (30.0 mmol) sodium cyanoborohydride in 10 ml methanol. After stirring overnight, 3.47 g (30.0 mmol) pyridine hydrochloride was added, and after 2 hour stirring sodium chloride was removed by filtration and the reaction mixture was concentrated to an oil. This was dissolved in 16 ml methanol and chromatographed on a 5×200 cm LH-20 column eluted with methanol. The product fraction contained 4.01 g (67.2%) of a mixture of diastereomers with NMR and mass spectra in accord with the assigned structure.

EXAMPLE 9

$N^\alpha$-[(pyridin-2-yl)methyl]Phe-O-t-Bu

A solution of 5.3 g (50.0 mmol) of pyridine-2-carboxaldehyde 5.16 g (20.0 mM), Phe-O-t-Bu.HCl and 1.56 g (18.3 mmol) sodium acetate in 250 ml methanol was treated over a 5 hour period with a solution of 1.89 g (30.0 mmol) sodium cyanoborohydride in 10 ml methanol. After stirring overnight 3.58 g (31 mmol) pyridine hydrochloride was added and the reaction mixture was concentrated to an oil. The oil was dissolved in 100 ml ethyl acetate extracted with 10 ml water, dried and reconcentrated. The oil was charged with 10 ml methanol to a 5×200 cm LH-20 column and eluted with methanol. The product containing fractions were concentrated to an oil which was rechromatographed over silica gel with hexane-ethyl acetate to give 1.04 g of product as an oil. NMR and mass spectra were in accord with the assigned structure.

EXAMPLE 10

Preparation of $N^\alpha$-[(pyridin-2-yl)methyl]Phe

To a slurry of L-phenylalanine (1.65 g; 10 mmol) in $H_2O$ (50 ml) was added a solution of pyridine 2-carboxaldehyde (5.36 g; 50 mmol) in $CH_3OH$ (50 ml), giving a clear, deeply-yellow solution. To this was added over a 3 hour period, a solution of $NaCNBH_3$ (1.89 g; 30 mmol) in $CH_3OH$ (15 ml). The resulting mixture was stirred for 4 hours, filtered, and treated with DOWEX-50 acidic resin (50 ml). The resin slurry was added to a column of DOWEX-50 (500 ml) in 1:1 $CH_3OH:H_2O$ and eluted with 4% pyridine in $CH_3OH:H_2O$ (1:1). The eluate was concentrated to a paste which was triturated with $CH_3OH$, giving the product (1.11 g; 30.5%), mp 215°–222° C. NMR and mass spectra were in accord with the assigned structure.

EXAMPLE 11

$N^\alpha$-[(Pyrrolidin-2-yl)methyl]Phe-O-t-Bu

To a solution of 5.71 g (60.0 mmol) Pyrrole-2-carboxaldehyde, 5.15 g (20.0 mmol) Phe-O-t-Bu.HCl and 1.48 g (18.1 mmol) sodium acetate under a nitrogen atmosphere in 100 ml methanol was added over a 4½ hour period a solution of 2.24 g (35.6 mmol) sodium cyanoborohydride in 8 ml of methanol. After stirring for an additional 60 hours, 4.10 g (36.0 mmol) pyridine hydrochloride was added and after 2 hour stirring, the reaction mixture was concentrated to a solid. Upon addition of 20 ml water and 20 ml ether a crystalline interphase formed, which was filtered, washed with water, ether and dried to yield 2.09 g (34.8%) of product with NMR and mass spectra in accord with the assigned structure.

EXAMPLE 12

$N^\alpha$-(Quinuclidin-3(RS)-yl)Nal-OCH$_3$.HCl

A solution of 2.20 g (8.28 mmol) of 3-(1-Naphthyl)-Ala-OCH$_3$.HCl and 4.02 g (25 mmol) of 3-Quinuclidinone hydrochloride in 30 ml of methanol was treated over the course of 11 hours with a solution of 1.20 g (20.7 mmol) of sodium cyanoborohydride in 7.5 ml of methanol. After the addition was complete the reaction mixture was allowed to stir for 4 days and then treated with 2.42 g (20.9 mmol) pyridine hydrochloride and after stirring for 3 hours, the solvent was removed using a rotary evaporator. The residue was stirred with 10 ml methanol and the insoluble sodium chloride was removed by filtration and washed with 5 ml methanol. The filtrate was treated with 60 ml ethyl acetate and the solution was seeded with 3-RS-quinuclidinol hydrochloride. The alcohol byproduct was removed by filtration and the filtrate was concentrated in vacuum to an oil. A second crop of this byproduct was removed by crystallization with a solvent mixture consisting of 50 ml ethyl acetate, 50 ml of acetonitrile, and 2 ml of methanol. The filtrate was concentrated in vacuo to 5.36 g of an amorphous residue. This was dissolved in 5 ml of methanol and chromatographed over a 5×200 cm column of LH-20 eluting with methanol. The product-containing fractions were combined and concentrated, yielding 4.4 g of product.

EXAMPLE 13

$N^\alpha$-(Quinuclidin-3(S)-yl)NaI-OCH$_3$.HCl

Using mixtures of acetonitrile and ether, for crystallization, a total of 440 mg of the 3(S)-diastereomer was obtained from the above mixture (Example 12).

EXAMPLE 14

$N^\alpha$-Methyl-$N^\alpha$-(quinuclidin-3(S)-yl)Phe-O-t-butyl

To a solution of $N^\alpha$-(quinuclidin-3(S)-yl)Phe-O-t-butyl (412 mg; 1.00 mmol) in CH$_3$OH (5 ml) was added 37% aqueous formaldehyde (0.375 ml; 5 equiv.). After 1.5 hours, NaCNBH$_3$ (189 mg; 3 equiv.) in CH$_3$OH (3 ml) was added over 10 hours. The reaction mixture was stirred for 7 days, and then pyridine hydrochloride (520 mg; 4.5 equiv.) was added, and the resulting mixture was stirred for 3 hours. The residue after evaporation of solvent was slurried in CHCl$_3$ and filtered. The filtrate was concentrated, and the residue was chromatographed on silica gel (eluting with EtOAc and then CHCl$_3$:CH$_3$OH:conc NH$_4$OH, 40:10:1), yielding the product (273 mg, 79%). $^1$H NMR (300 MHz, CD$_3$OD) 1.5(9H,s), 1.5-1.65(1H,m); 1.7-1.9(2H,m); 1.9-2.05(1H,m); 2.2-2.3(2H,m); 2.35(3H,s); 2.4-2.5(1H,dd); 2.8-3.3(7H,m); 3.4(1H,dd), 7.15-7.25(5H,m). FAB mass spectrum, m/e 345 (M++1).

EXAMPLE 15

$N^\alpha$-[2(RS)-Ethoxycarbonylquinuclidin-3(RS)-yl]-Phe-O-t-Bu.HCl

A solution of 5.4 g (27.4 mmol) Ethyl-Quinuclidin-3-one-2-carboxylate hydrochloride and 2.43 g (10.98 mmol) Phe-O-t-Bu in 140 ml ethanol was treated over a 18 hour period with a solution of 1.03 g (16.4 mmol) sodium cyanoborohydride in 10 ml ethanol. After stirring for an additional 70 hours, 6.24 g (54 mmol) pyridine hydrochloride was added. After stirring for one hour, sodium chloride was removed by filtration and the filtrate was concentrated to an amorphous mass. On treatment with 50 ml acetonitrile 1.44 g (50.9%) of unreacted Phe-O-t-Bu crystallized as the hydrochloride. The acetonitrile was removed to give a residue which was charged in 10 ml methanol to a 5×200 cm LH-20 column and eluted with methanol. The product-containing fraction yielded 1.59 g (33.4%) of material with NMR and mass spectra in accord with the assigned structure.

EXAMPLE 16

Boc-ACHPA-Ile-NHCH$_2$(pyridin-4-yl) ·

Boc-ACHPA-NHNH$_2$ was prepared from Boc-ACHPA-OEt by treatment with 5 equiv. of anhydrous NH$_2$NH$_2$ in EtOH. To a solution of Boc-ACHPA-NHNH$_2$ (0.912 g, 2.828 mmol) in DMF (10 ml) at −30° C., conc. HCl (0.943 ml, 5.6558 mmol) was added, followed by the addition of isoamylnitrite (0.465 ml, 3.34 mmol). The mixture was stirred for 3 hours at −20° C., and a solution of hydrochloride salt of Ile-NHCH$_2$(pyridine-4-yl) (0.801 g, 3.11 mmol) (obtained from Boc-Ile-NHCH$_2$(pyridin-4-yl) after conc. HCl treatment at room temperature) and diisopropylethylamine (1.7 ml) in DMF (5 ml) was added. The mixture was then warmed up to −5° C. and stirred at that temperature for 3 days. DMF was partially removed in vacuo, and the residue was treated with cold water and extracted with ethylacetate. The organic phase was washed with water and then dried (MgSO$_4$). The solvent was evaporated in vacuo and the crude product, thus obtained, was purified by flash column chromatography (silica-gel) using CHCl$_3$:CH$_3$OH:NH$_4$OH (100:10:1) to give the desired product as a foam (0.63 g). $^1$H NMR (CD$_3$OD) and FAB mass spectral data were consistent with the desired structure.

EXAMPLE 17

Boc-Nle-ACHPA-Ile-NHCH$_2$(pyridin-4-yl)

Boc-ACHPA-Ile-NHCH$_2$(pyridine-4-yl) (0.228 g, 0.44 mmol) was deprotected by treatment with saturated HCl/CH$_3$OH (5 ml) at room temperature for 1 hour. Removal of solvent in vacuo and drying the residue over P$_2$O$_5$ gave desired hydrochloride salt of Nle-ACHPA-Ile-NHCH$_2$-(pyridine-4-yl). The above material was dissolved in dry DMF (5 ml), and diisopropylethylamine (0.077 ml) was added to liberate the free amine. The amine solution was then added to a mixture of Boc-Nle-OH (0.112 g, 0.4838 mmol), DCC (0.109 g, 0.53 mmol) and HOBT (0.09 g, 0.66 mmol) in DMF (3 ml). The resulting mixture was stirred at 25° C. for 24 hours. The reaction was filtered, and the filtrate was concentrated in vacuo. The residue was purified on a LH-20 column using methanol as eluant. The major component from LH-20 column was then purified by flash chromatography using CHCl$_3$:CH$_3$OH:NH$_4$OH (100:10:1) to give the pure product as a foam (0.163 g). The product gave satisfactory $^1$H NMR and FAB mass spectra for the desired product.

EXAMPLE 18

$N^\alpha$-Boc-His(DNP)-ACHPA-Ile-NHCH$_2$(pyridin-4-yl)

This material was prepared by using the procedure in Example 17, and replacing Boc-Nle with $N^\alpha$-Boc-His(DNP). NMR and mass spectra were in accord with the assigned structure.

EXAMPLE 19

His(DNP)-ACHPA-Ile-NHCH$_2$(pyridin-4-yl)

This compound was prepared by treatment of the product of Example 18 with anhydrous HCl in CH$_3$OH, followed by liberation of the free amine with diisopropylethylamine. NMR and mass spectra were in accord with the assigned structure.

EXAMPLE 20

$N^\alpha$-(quinuclidin-3-yl)Phe-Nle-ACHPA-Ile-AMP

Boc-Nle-ACHPA-Ile-AMP (0.163 g) was deprotected by treatment with saturated HCl/CH$_3$OH (5 ml) at room temperature for 1 hour. Removal of solvent in vacuo gave desired hydrochloride salt of Nle-ACHPA-Ile-NHCH$_2$(pyridine-4-yl). The above material was dissolved in dry DMF (5 ml) and was treated with diisopropylethylamine (0.14 ml) to liberate the free amine. The amine solution was then added to a mixture of $N^\alpha$-(quinuclidin-3(S)-yl)Phe (0.104 g), DCC (0.077 g) and HOBT (0.063 g) in DMF (5 ml). The resulting mixture was stirred at room temperature for 24 hours. The reaction was filtered, and the filtrate was concentrated in vacuo. The residue was purified on an LH-20 column using methanol. The major component from LH-20 column was then purified by flash chromatography using CHCl$_3$:CH$_3$OH:NH$_4$OH (100:10:1) to give the pure product as a foam (0.055 g). The product gave satisfactory $^1$H NMR and FAB mass spectra for the desired product. IC$_{50}$=5.0 nM.

EXAMPLE 21

N$^\alpha$-Methyl-N$^\alpha$-(quinuclidin-3(S)-yl)Phe-Nle-ACHPA-Ile-NHCH$_2$(pyridin-4-yl)

The titled compound was prepared according to the procedure described for the above compound, by coupling N$^\alpha$-methyl-N$^\alpha$-(quinuclidin-3(S)-yl)Phe (0.0174 g) with Nle-ACHPA-Ile-NHCH$_2$(pyridine-4-yl) (0.0292 g) in presence of EDC (0.0111 g) and HOBT (0.0098 g). The pure product isolated after flash chromatography using CHCl$_3$:CH$_3$OH:NH$_4$OH (100:10:1), giving 0.0292 g of product as a foam. The material gave satisfactory $^1$H NMR and FAB mass spectra (M+H=802) for the desired product. IC$_{50}$=150 nM.

EXAMPLE 22

[N$^\alpha$-(N-Methylquinuclidin-3(S)-yl)Phe-His(DNP)-ACHPA-Ile-NH-CH$_2$-(pyridin-4-yl)]+I$^-$ A solution of 365.5 mg (0.506 mmol) His-(DNP)-ACHPA-Ile-NHCH$_2$(pyridin-4-yl) and 251.4 mg (0.604 mmol) of the product of Example 5 with 81.4 mg (0.602 mmol) N-hydroxybenztriazole in 5 ml DMF at 0° C. was treated with 148 mg (0.717 mmol) Dicyclohexylcarbodiimide in 4 ml dimethoxyethane. The mixture was stirred at room temperature for 70 hours, concentrated in vacuo, treated with 20 ml water and lyophilized. The residue was treated with 5 ml methanol and filtered from dicyclohexylurea. The filtrate was concentrated again, taken up in methanol and chromatographed on a 2.5×210 cm column of LH-20. The product-containing fractions yielded 351.7 mg (62.0%) of material with consistent NMR and mass spectra.

EXAMPLE 23

[N$^\alpha$-(N-Methylquinuclidin-3(S)-yl)Phe-His-ACHPA-Ile-NH-CH$_2$-(pyridin-4-yl)]+I$^-$ The DNP protecting group was removed from the product of Example 6 by treating 346.7 mg (0.310 mmol) of material with 5 ml 0.25 molar thiophenol and 0.5 ml methanol. After stirring overnight, byproduct was removed by filtration and the filtrate was concentrated in vacuo. The residue was dissolved in methanol (1 ml) and chromatographed on a 0.9×210 cm column of LH-20 to give 220 mg of material with NMR and mass spectra in accord with the assigned structure. IC$_{50}$=1.7 nM.

EXAMPLE 24

N$^\alpha$-(Quinuclidin-3-yl)Phe-His-ACHPA-Ile-NHCH$_2$(pyridin-4-yl)

To a solution of 0.21 g (3.0 mmol) of His(DNP)-ACHPA-Ile-NHCH$_2$(pyridin-4-yl) (Example 19) in 2 ml of DMF at 0° C. were added sequentially 0.044 g (3.3 mmol) of N-hydroxybenzotriazole hydrate followed by 0.10 g (3.0 mmol) of N$^\alpha$-(quinuclidin-3-yl)Phe.HCl (first eluted diastereomer of RS mixture on Dynamax C18 HPLC column eluting with 50% CH$_3$CN/H$_2$O/0.1% TFA) and 0.068 g (3.3 mmol) of DCC. The mixture was stirred at room temperature overnight and then concentrated in vacuo. The residue was applied to a 15 cm×2 cm flash chromatography SiO$_2$ column and eluted with 85:14:1 CHCl$_3$:MeOH:NH$_4$OH to give 0.25 g of a pale yellow solid. 87% yield. To a solution of the above protected peptide (0.25 mmol) in 3 ml of dry CH$_2$Cl$_2$ was added 0.11 g (1.02 mmol) of thiophenol. The reaction mixture was stirred overnight at room temperature and then concentrated in vacuo. The residue was applied to a 2.5 cm×200 cm LH-20 column and eluted with MeOH at 4 ml/min to give 0.15 g (0.18 mmol) of the desired peptide. Characteristic $^1$H NMR signals (300 MHz, CD$_3$OD): 0.8 (3H, t); 0.89 (3H, d); 2.29 (2H, d); 2.45 (1H, dt); 2.63 (1H, dd); 3.90 (1H, dt); 4.15 (1H, d); 4.39 (2H, dd); 4.50 (1H, t); 6.89 and 7.65 (1H, s); 7.10–7.21 (5H, m); 7.30 (2H, d). Fast atom bombardment mass spectrum gave 812 for M+ +H=812, calculated for C$_{45}$H$_{65}$N$_3$O$_4$. IC$_{50}$=2.0 nM.

EXAMPLE 25

(2S,4S,5S)-Boc-Cal[CH(OH)CH$_2$]Val-NH-n-butyl

To a solution of 0.2 g (2.8 mmol) of n-butyl amine in 5 ml of dry CH$_2$Cl$_2$ at 0° C. under N$_2$ was added 1.4 ml of a 2.0M (2.8 mmol) solution of trimethyl aluminum in toluene dropwise. After 15 minutes 0.5 g (1.46 mmol) of (2S,4S,5S)-Boc-Cal[CH(OH)CH$_2$]Val lactone was added as a solid. The reaction mixture was warmed to 30° C. and monitored by TLC (50% EtAc/hexane) for the consumption of the starting material. The reaction mixture was diluted with 50 ml of EtAc and washed with 1N HCl (3×10 ml) and sat. NaHCO$_3$ (2×10 ml), and dried over MgSO$_4$. The solution was filtered and concentrated in vacuo. The residue was purified by MPLC on a SiO$_2$ Lobar C column eluting with 50% EtAc/hexanes. A single fraction was collected as a colorless oil. 0.5 g (1.17 mmol), 80% yield. $^1$H-NMR (300 MHz, CDCl$_3$): 1.80–1.92 (9H, m), 1.40 (9H, s), 1.05–1.90 (20H, m), 2.03 (1H, m), 3.12 (1H, m), 3.22 (1h, m), 3.45 (2H, bm), 4.15 (1H, bd), 4.79 (1H, bd), 6.30 (2H, bt). FAB m.s.=427 for M+ +H. Anal. (C$_{24}$H$_{46}$N$_2$O$_4$): C,H,N.

EXAMPLE 26

His-Cal[CH(OH)CH$_2$]Val-NH-n-butyl

To 0.5 g (1.17 mmol) of Boc-Cal[CH(OH)CH$_2$]Val-NH-n-butyl in 3 ml of dry CH$_2$Cl$_2$ was added at 0° C. 0.5 ml of trifluoroacetic acid. The reaction mixture was stirred for 4 hours and concentrated in vacuo. The residue was dissolved in 50 ml of CH$_2$Cl$_2$ and washed with 1N NaOH (2×10 ml), sat. NaCl solution (1×10 ml) and dried over MgSO$_4$. The solution was filtered and concentrated in vacuo. The residue was dissolved in 3 ml of CH$_2$Cl$_2$ and treated sequentially with 0.46 g (1.28 mmol) of N$^\alpha$, N$^\pi$-(Boc)$_2$His, 0.17 g (1.28 mmol) HOBt and 0.26 g (1.28 mmol) of DCC. The reaction mixture was stirred for 48 hours, diluted with 20 ml EtOAc, filtered and the filtrate washed with sat. NaHCO$_3$ solution (2×10 ml) and sat. NaCl solution (1×10 ml). The organic phase was dried over MgSO$_4$, filtered and concentrated in vacuo. The residue was purified by MPLC on SiO$_2$ Lobar B column eluting with 95:5:0.01 CHCl$_3$:MeOH:NH$_4$OH. For complete purification the recovered material was rechromatographed under identical conditions to give 0.43 g (0.64 mmol) of N$^\alpha$, N$^\pi$-(Boc)$_2$His-Cal[CH(OH)CH$_2$]Val-NH-n-butyl. This material was dissolved in 2 ml of CH$_2$Cl$_2$ and cooled to 0° C. and treated with 2 ml of trifluoroacetic acid. The reaction mixture was allowed to warm to room temperature and stirred overnight and concentrated in vacuo. The residue was dissolved in 15 ml of CH$_2$Cl$_2$ and washed with 1N NaOH (2×5 ml). The organic phase was dried over MgSO₄, filtered and concentrated to give 0.22 g (0.48 mmol) of a glass (75% yield). Characteristic $^1$H-NMR (360 MHz CD₃OD) signals: 0.7-0.95 (m), 1.0-0.8 (m), 2.10 (1H, 1H), 2.69 (1H, m), 2.92 (1H, dd), 3.0-3.15 (2H, m), 3.22-3.40 (1H, m), 3.49 (1H, bt), 3.78 (1H, m), 6.80 (1H, s), 7.50 (1H, s).

EXAMPLE 27

$N^\alpha$-(Quinuclidin-3(S)-yl)Phe-His-Cal[CH(OH)CH₂]-Val-NH-n-butyl

To a solution of 0.061 g (0.13 mmol) of His-Cal[CH(OH)CH₂]Val-NH-n-butyl dissolved in 1 ml of DMF at 0° C. was added 19.2 mg (0.14 mmol) of N-hydroxybenzotriazole followed by 0.058 g (0.14 mmol) of $N^\alpha$-(quinuclidin-3(S)-yl)Phe.HCl and 29 mg (0.14 mmol) of DCC. The reaction mixture was stirred overnight at room temperature and then concentrated in vacuo. The residue was dissolved in MeOH and filtered, the filtrate was applied to an LH-20 2.0 cm×80 cm column and eluted with MeOH. The first product to elute was collected and concentrated in vacuo. The oily product was further purified by SiO₂ flash chromatography eluting with 85:14:1 CHCl₃:MeOH:NH₄OH to give 0.07 g of the desired peptide (75% yield). Characteristic $^1$H-NMR signals (300 MHz, CD₃OD): 0.75-0.92 (9H, m); 4.60 (1H, s); 7.1-7.3 (5H, m); 7.30 and 8.75 (1H, s); 7.65 (1H, d). Fast atom bombardment mass spectrum gave 722 for M⁺+H, calculated for M⁺=C₄₁H₆₅N₇O₄. IC₅₀=1.4 nM.

EXAMPLE 28

NorACHPA-OEt hydrochloride

A solution of Boc-norACHPA-OCH₃ (500 mg; 1.59 mmol) in EtOH (20 ml) was saturated with anhydrous HCl and left to stand (72 hours). Concentration and reconcentration from CCl₄ provided the product (422 mg). $^1$H NMR (300 MHz, CD₃OD): 0.9-1.8(m,13H); 1.30(3H,t); 3.55-3.65(1H,m); 4.2-4.3(3H,m).

EXAMPLE 29

Boc-Nle-norACHPA-OEt hydrochloride

To a cold (ice-bath) solution of norACHPA-OEt.HCl (211 mg; 0.794 mmol) in CH₂Cl₂ (3 ml) was added Et₃N (0.133 ml; 1.5 equiv.), Boc-Nle (275 mg; 1.5 equiv.), HOBT (182 mg; 1.5 equiv.) and EDC (228 mg; 1.5 equiv). The reaction mixture was stirred (18 hours) and then allowed to warm to room temperature. The mixture was poured into EtOAc and washed with H₂O, 1N HCl, satd. NaHCO₃ and brine and dried (MgSO₄). Concentration gave the crude product which was used in the next step without purification. $^1$H NMR (300 MHz, CD₃OD): 0.8-1.8(22H,m); 1.30(3H,t); 1.45(9H,s); 3.9-4.0(1H,dd); 4.1-4.3(3H,m); 4.5-4.6(1H,m). FAB mass spectrum m/e 443 (M⁺+1).

EXAMPLE 30

$N^\alpha$-(Quinuclidin-3(S)-yl)Phe-Nle-norACHPA-OEt

A solution of Boc-Nle-norACHPA-OEt (343 mg; 0.775 mmol) in anhydrous TFA (4 ml) and CH₂Cl₂ (4 ml) was allowed to stand for 45 minutes, then concentrated to dryness, giving Nle-norACHPA-OEt (381 mg) as the trifluoroacetate salt. To a cold (ice-bath) solution of a portion (133 mg; 0.388 mmol) of this material in CH₂Cl₂ (3 ml) was added Et₃N (0.172 ml; 3.2 equiv.), $N^\alpha$-(quinuclidin-3(S)-yl)Phe.HCl (202 mg; 1.5 equiv.), HOBT (89 mg; 1.5 equiv.) and EDC (112 mg; 1.5 equiv.). The reaction mixture was stirred for 3 hours at 0° C. and for 60 hours at room temperature. The mixture was then diluted with EtOAc (50 ml) and washed with H₂O. The product was extracted into 1N HCl, and precipitated upon neutralization with Na₂CO₃ (132 mg; 57%). IC₅₀=91 nM.

EXAMPLE 31

$N^\alpha$-[(pyridin-2-yl)methyl]Phe-His-ACHPA-Ile-NHCH₂(pyridin-4-yl)

A reaction mixture containing 154.2 mg (0.602 mmol) of the product of Example 10, 362.0 mg (0.502 mM) His(DNP)-ACHPA-Ile-NHCH₂(pyridin-4-yl), 82.1 mg (0.608 mM) N-hydroxybenztriazole and 124 mg (0.601 mM) dicyclohexylcarbodiimide in 5 ml dimethoxyethane and 6 ml DMF was stirred at room temperature for 4 hour and then concentrated. The residue was taken up in 20 ml methylene chloride, filtered from dicyclohexylurea and washed with 3×15 ml ½ saturated bicarbonate solution. After removal of the solvent the residue was charged with 2 ml methanol to a 2.5×210 cm column of LH-20 and eluted with methanol. The product containing fractions contained 318 mg of material. This was treated with 4 ml of 0.25M thiophenol in methylene chloride. The next day the solvent was removed in vacuo and the byproduct was crystallized from 2 ml ice-cold methanol and removed by filtration. The filtrate was charged to a 0.9×210 cm LH-20 column and eluted with methanol and the impure product obtained was rechromatographed over silica gel with mixture of methylene chloride, methanol and concentrated aqueous ammonia in a 90:9:1 ratio. The product fraction contained 46.8 mg (11.7%) of material with NMR and mass spectrum in accord with the expected structure. IC₅₀=7 nM.

The pharmaceutically-acceptable salts of the peptides of Formula I (in the form of water- or oil-soluble or dispersible products) include the conventional non-toxic salts or the quarternary ammonium salts of these peptides which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The novel peptides of the present invention possess a high degree of activity in treating renin-associated hypertension, hyperaldosteronism and/or congestive heart failure in humans, as well as in other warm-blooded animals such as mice, rats, horses, dogs and cats.

For these purposes, the peptides of the present invention may be administered orally, parenterally (including subcutaneous injections, intravenous, intramuscular, intrasternal injection or infusion techniques), by inhalation spray, or rectally, in dosage unit formulations containing conventional non-toxic, pharmaceutically-acceptable carriers, adjuvants and vehicles.

Thus, in accordance with the present invention there is further provided a method of treating and a pharmaceutical composition for treating renin-associated hypertension, hyperaldosteronism, and/or congestive heart failure. This treatment involves administering to a patient in need of such treatment a pharmaceutical composition comprising a pharmaceutical carrier, optionally with an adjuvant, and a therapeutically-effective amount of a peptide selected from those peptides defined in I.

These pharmaceutical compositions may be in the form of orally-administrable suspensions or tablets; nasal sprays; sterile injectable preparations, for example, as sterile injectable aqueous or oleagenous suspensions; or suppositories.

When administered orally as a suspension, these compositions may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquify and/or dissolve in the rectal cavity to release the drug.

Dosage levels of the order of 0.02 to 2.0 grams-per-day are useful in the treatment of the above-indicated conditions, with oral doses two-to-five times higher. For example, renin-associated hypertension and hyperaldosteronism are effectively treated by the administration of from 10 to 50 milligrams of the compound per kilogram of body weight from one to three times per day. It will be understood, however, that the specific dose level and frequency of dosage for any particular patient will depend upon a variety of factors including the activity of the specific compound employed, the metabolic stability and length of action of that compound, the age, body weight, general health, sex, diet, mode and time of administration, rate of excretion, drug combination the severity of the particular condition, and the host undergoing therapy.

The present invention is also directed to combinations of the novel renin-inhibitory peptides of Formula I with one or more antihypertensive agents selected from the group consisting of diuretics, a- and/or β-adrenergic blocking agents, CNS-acting agents, adrenergic neuron blocking agents, vasodilators, angiotensin I converting enzyme inhibitors, calcium channel blockers, and other antihypertensive agents.

For example, the compounds of this invention can be given in combination with such compounds or salt or other derivative forms thereof as:

Diuretics: acetazolamide; amiloride; bendroflumethiazide; benzthiazide; bumetanide; chlorothiazide; chlorthalidone; cyclothiazide; ethacrynic acid; furosemide; hydrochlorothiazide; hydroflumethiazide; indacrinone (racemic mixture, or as either the (+) or (−) enantiomer alone, or a manipulated ratio, e.g., 9:1 of said enantiomers, respectively); metolazone; methyclothiazide; muzolimine; polythiazide; quinethazone; sodium ethacrynate; sodium nitroprusside; spironolactone; ticrynafen; triamterene; trichlormethiazide;

α-Adrenergic Blocking Agents: dibenamine; phentolamine; phenoxybenzamine; prazosin; tolazoline;

β-Adrenergic Blocking Agents: atenolol; metoprolol; nadolol; propranolol; timolol;

((±)-2-[3-(tert-butylamino)-2-hydroxypropoxy]-2-furananilide) (ancarolol);

(2-acetyl-7-(2-hydroxy-3-isopropylaminopropoxy)benzofuran HCl) (befunolol);

((±)-1-(isopropylamino)-3-(p-(2-cyclopropylmethoxyethyl)-phenoxy)-2-propanol HCl) (betaxolol);

(1-[(3,4-dimethoxyphenethyl)amino]-3-(m-tolyloxy)-2-propanol HCl) (bevantolol);

((±)-1-(4-(2-isopropoxyethoxy)methyl)phenoxy)-3-isopropylamino-2-propanol)fumarate) (bisoprolol);

(4-(2-hydroxy-3-[4-(phenoxymethyl)-piperidino]-propoxy)-indole);

(carbazolyl-4-oxy-5,2-(2-methoxyphenoxy)-ethylamino-2-propanol);

(1-((1,1-dimethylethyl)amino)-3-((2-methyl-1H-indol-4-yl)oxy)-2-propanol benzoate) (bopindolol);

(1-(2-exobicyclo[2.2.1]-hept-2-ylphenoxy)-3-[(1-methylethyl)-amino]-2-propanol HCl) (bornaprolol);

(o-[2-hydroxy-3-[(2-indol-3-yl-1,1-dimethylethyl)amino]propoxy]benzonitrile HCl) (bucindolol);

(α-[(tert.butylamino)methyl]-7-ethyl-2-benzofuranmethanol) (bufuralol);

(3-[3-acetyl-4-[3-(tert.butylamino)-2-hydroxypropyl]-phenyl]-1,1-diethylurea HCl) (celiprolol);

((±)-2-[2-[3-[(1,1-dimethylethyl)amino]-2-hydroxypropoxy]phenoxy]-N-methylacetamide HCl) (cetamolol);

(2-benzimidazolyl-phenyl(2-isopropylaminopropanol));

((±)-3'-acetyl-4'-(2-hydroxy-3-isopropylaminopropoxy)acetanilide HCl) (diacetolol);

(methyl-4-[2-hydroxy-3-[(1-methylethyl)aminopropoxy]]benzenepropanoate HCl) (esmolol);

(erythro-DL-1-(7-methylindan-4-yloxy)-3-isopropylaminobutan-2-ol);

(1-(tert.butylamino)-3-[0-(2-propynyloxy)phenoxy]-2-propanol (pargolol);

(1-(tert.butylamino)-3-[o-(6-hydrazino-3-pyridazinyl)-phenoxy]-2-propanol diHCl) (prizidilol);
((−)-2-hydroxy-5-[(R)-1-hydroxy-2-[(R)-(1-methyl-3-phenylpropyl)amino]ethyl]benzamide);
(4-hydroxy-9-[2-hydroxy-3-(isopropylamino)-propoxy]-7-methyl-5H-furo[3,2-g][1]-benzopyran-5-one) (iprocrolol);
((−)-5-[(tert.butylamino)-2-hydroxypropoxy]-3,4-dihydro-1-(2H)-naphthalenone HCl) (levobunolol);
(4-(2-hydroxy-3-isopropylamino-propoxy)-1,2-benzisothiazole HCl);
(4-[3-(tert.butylamino)-2-hydroxypropoxy]-N-methylisocarbostyril HCl);
((±)-N-2-[4-(2-hydroxy-3-isopropyl aminopropoxy)-phenyl]ethyl-N'-isopropylurea) (pafenolol);
(3-[[(2-trifluoroacetamido)ethyl]amino]-1-phenoxypropan-2-ol);
(N-(3-(o-chlorophenoxy)-2-hydroxypropyl)-N'-(4'-chloro-2,3-dihydro-3-oxo-5-pyridazinyl)ethylenediamine);
((±)-N-[3-acetyl-4-[2-hydroxy-3-[(1-methylethyl)amino]-propoxy]phenyl]butanamide) (acebutolol);
((±)-4'-[3-(tert-butylamino)-2-hydroxypropoxy]spiro[cyclohexane-1,2'-indan]-1'-one) (spirendolol);
(7-[3-[[2-hydroxy-3-[(2-methylindol-4-yl)oxy]propyl]amino]butyl]thiophylline) (teoprolol);
((±)-1-tert.butylamino-3-(thiochroman-8-yloxy)-2-propanol) (tertatolol);
((±)-1-tert.butylamino-3-(2,3-xylyloxy)-2-propanol HCl) (xibenolol);
(8-[3-(tert.butylamino)-2-hydroxypropoxy]-5-methylcoumarin) (bucumolol);
(2-(3-(tert.butylamino)-2-hydroxy-propoxy)benzonitrile HCl) (bunitrolol);
((±)-2'-[3-(tert-butylamino)-2-hydroxypropoxy-5'-fluorobutyrophenone) (butofilolol);
(1-(carbazol-4-yloxy)-3-(isopropylamino)-2-propanol) (carazolol);
(5-(3-tert.butylamino-2-hydroxy)propoxy-3,4-dihydrocarbostyril HCl) (carteolol);
(1-(tert.butylamino)-3-(2,5-dichlorophenoxy)-2-propanol) (cloranolol);
(1-(inden-4(or 7)-yloxy-3-(isopropylamino)-2-propanol HCl) (indenolol);
(1-isopropylamino-3-[(2-methylindol-4-yl)oxy]-2-propanol) (mepindolol);
(1-(4-acetoxy-2,3,5-trimethylphenoxy)-3-isopropylaminopropan-2-ol) (metipranolol);
(1-(isopropylamino)-3-(o-methoxyphenoxy)-3-[(1-methylethyl)amino]-2-propanol) (moprolol);
((1-tert.butylamino)-3-[(5,6,7,8-tetrahydro-cis-6,7-dihydroxy-1-naphthyl)oxy]-2-propanol) (nadolol);
((S)-1-(2-cyclopentylphenoxy)-3-[(1,1-dimethylethyl)amino]-2-propanol sulfate (2:1)) (penbutolol);
(4'-[1-hydroxy-2-(amino)ethyl]methanesulfonanilide) (sotalol);
(2-methyl-3-[4-(2-hydroxy-3-tert.butylaminopropoxy)-phenyl]-7-methoxy-isoquinolin-1-(2H)-one);
(1-(4-(2-(4-fluorophenyloxy)ethoxy)phenoxy)-3-isopropylamino-2-propanol HCl);
((−)-p-[3-[(3,4-dimethoxyphenethyl)amino]-2-hydroxypropoxy]-β-methylcinnamonitrile) (pacrinolol);
((±)-2-(3'-tert.butylamino-2'-hydroxypropylthio)-4-(5'-carbamoyl-2'-thienyl)thiazole HCl) (arotinolol);
((±)-1-[p-[2-(cyclopropylmethoxy)ethoxy]phenoxy]-3-(isopropylamino)-2-propanol) (cicloprolol);
((±)-1-[(3-chloro-2-methylindol-4-yl)oxy]-3-[(2-phenoxyethyl)amino]-2-propanol) (indopanolol);

((±)-6-[[2-[[3-(p-butoxyphenoxy)-2-hydroxypropyl]amino]ethyl]amino]-1,3-dimethyluracil) (pirepolol);
(4-(cyclohexylamino)-1-(1-naphtholenyloxy)-2-butanol);
(1-phenyl-3-[2-[3-(2-cyanophenoxy)-2-hydroxypropyl]aminoethyl]hydantoin HCl);
(3,4-dihydro-8-(2-hydroxy-3-isopropylaminopropoxy)-3-nitroxy-2H-1-benzopyran) (nipradolol);

α- and β-Adrenergic Blocking Agents:

((±)-1-tert-butylamino-3-[o-[2-(3-methyl-5-isoxazolyl)vinyl]phenoxy]-2-propanol) (isoxaprolol);
(1-isopropylamino-3-(4-(2-nitroxyethoxy)phenoxy)-2-propanol HCl);
(4-hydroxy-α-[[3-(4-methoxyphenyl)-1-methylpropyl]aminomethyl]-3-(methylsulfinyl)-benzmethanol HCl) (sulfinalol);
(5-[1-hydroxy-2-[[2-(o-methoxyphenoxy)ethyl]amino]ethyl]-2-methylbenzenesulfonamide HCl);
(5-[1-hydroxy-2-[(1-methyl-3-phenylpropyl)amino]ethyl]salicylamide HCl) (labetalol);
(1-((3-chloro-2-methyl-1H-indol-4-yl)oxy)-3-((2-phenoxyethyl)amino)-2-propanol-hydrogenmalonate) (ifendolol);
(4-(2-hydroxy-3-[(1-methyl-3-phenylpropyl)amino]propoxy)benzeneacetamide);
(1-[3-[[3-(1-naphthoxy)-2-hydroxypropyl]-amino]-3,3-dimethyl-propyl]-2-benzimidazolinone);
(3-(1-(2-hydroxy-2-(4-chlorophenylethyl)-4-piperidyl)-3,4-dihydroxy)quinoxolin-2(1H)-one);

CNS-Acting Agents: clonidine; methyldopa;
Adrenergic Neuron Blocking Agents: guanethidine; reserpine and other rauwolfia alkaloids such as rescinnamine;
Vasodilators: diazoxide; hydralazine; minoxidil;
Angiotensin I Converting Enzyme Inhibitors:

1-(3-mercapto-2-methyl-1-oxopropyl)-L-proline (captopril);
(1-(4-ethoxycarbonyl-2,4(R,R)-dimethylbutanoyl)indoline-2(S)-carboxylic acid);
(2-[2-[[1-(ethoxycarbonyl)-3-phenyl-propyl]amino]-1-oxopropyl]-1,2,3,4-tetrahydro-3-isoquinoline carboxylic acid);
((S)-1-[2-[[1-(ethoxycarbonyl)-3-phenylpropyl]amino]-1-oxopropyl]octahydro-1H-indole-2-carboxylic acid HCl);
(N-cyclopentyl-N-(3-(2,2-dimethyl-1-oxopropyl)thiol-2-methyl-1-oxopropyl)glycine) (pivapril);
((2R,4R)-2-(2-hydroxyphenyl)-3-(3-mercaptopropionyl)-4-thiazolidinecarboxylic acid);
(1-(N-[1(S)-ethoxycarbonyl-3-phenylpropyl]-(S)-alanyl)cis,syn-octahydroindol-2(S)-carboxylic acid HCl);
((−)-(S)-1-[(S)-3-mercapto-2-methyl-1-oxopropyl]indoline-2-carboxylic acid);
([1(S),4S]-1-[3-(benzoylthio)-2-methyl-1-oxopropyl]-4-phenylthio-L-proline;
(3-([1-ethoxycarbonyl-3-phenyl-(1S)-propyl]amino)-2,3,4,5-tetrahydro-2-oxo-1-(3S)-benzazepine-1-acetic acid HCl);
(N-(2-benzyl-3-mercaptopropanoyl)-S-ethyl-L-cysteine) and the S-methyl analogue;
(N-(1(S)-ethoxycarbonyl-3-phenylpropyl)-L-alanyl-L-proline maleate) (enalapril);
N-[1-(S)-carboxy-3-phenylpropyl]-L-alanyl-1-proline;

N²-[1-(S)-carboxy-3-phenylpropyl]-L-lysyl-L-proline (lysinopril);

Calcium Channel Blockers:

α-[3-[[2-(3,4-dimethoxyphenyl)ethyl]methylamino]-propyl]-3,4-dimethoxy-α-(1-methylethyl)benzeneacetonitrile (verapamil);
1,4-dihydro-2,6-dimethyl-4-(2-nitrophenyl)-3,5-pyridinedicarboxylic acid dimethyl ester (nifedipine);
2-(2,2-dicyclohexylethyl)piperidine (perhexiline);
N-(1-methyl-2-phenylethyl)-phenylbenzenepropanamine (prenylamine);
3-(aminosulfonyl)-4-chloro-N-(2,3-dihydro-2-methyl-1H-indol-1-yl)benzamide (indapamide);
(2'-(2-diethylaminoethoxy)-3-phenylpropiophenone (etafenone);
(4-[4,4-bis-(4-fluorophenyl)butyl]-N-(2,6-dimethylphenyl)-1-piperazineacetamide) (lidoflazine);
(2-(N-benzyl-N-methylamino)ethylmethyl-2,6-dimethyl-4-(m-nitrophenyl)-1,4-dihydro-3,5-pyridinedicarboxylate HCl) (nicardipine);
(N-(3,4-dimethoxyphenethyl)-2-(3,4-dimethoxyphenyl)-N-methyl-m-dithiane-2-propylamine-1,1,3,3-tetraoxide) (tiapamil);
(5,6-dimethoxy-2-(3-[(α-(3,4-dimethoxy)phenylethyl)-methylamino]propyl)phthalimidine) (falipamil);
(β-[(2-methylpropoxy)methyl]-N-phenyl-N-phenylmethyl-1-pyrrolidineethanamine HCl monohydrate) (bepridil);
((+)-cis-3-(acetyloxy)-5-[2-(dimethylamino)ethyl]-2,3-dihydro-2-(4-methoxyphenyl)-1,5-benzothiazepin-4-(5H)-one) (diltiazem);
((E)-1-[bis-(p-fluorophenyl)methyl]-4-cinnamylpiperazine di HCl) (flunarizine);
(5-[(3,4-dimethoxyphenethyl)methylamino]-2-isopropyl-2-(3,4,5-trimethoxyphenyl)valeronitrile (gallopamil);
(ethylmethyl(2,3-dichlorophenyl)-1,4-dihydro-2,6-dimethyl-3,5-pyridinedicarboxylate (felodipine);
(isopropyl-2-methoxyethyl-1,4-dihydro-2,6-dimethyl-4-(3-nitrophenyl)-3,5-pyridinecarboxylate) (nimodipine);
(3-ethyl-5-methyl-1,4-dihydro-2,6-dimethyl-4-(3-nitrophenyl)-3,5-pyridine-dicarboxylate) (nitrendipine);

Other Antihypertensive Agents: aminophylline; cryptenamine acetates and tannates; deserpidine; meremethoxylline procaine; pargyline; trimethaphan camsylate; and the like, as well as admixtures and combinations thereof.

Typically, the individual daily dosages for these combinations can range from about one-fifth of the minimally-recommended clinical dosages to the maximum recommended levels for the entities when they are given alone. Coadministration is most readily accomplished by combining the active ingredients into a suitable unit dosage form containing the proper dosages of each. Other methods of coadministration are, of course, possible.

The renin-inhibitory novel peptides of the present invention may also be utilized in in vivo or in vitro diagnostic methods for the purpose of establishing the significance of renin as a causative or contributory factor in hypertension, hyperaldosteronism or congestive heart failure in a particular patient.

In the in vivo method, a novel peptide of the present invention is administered to a patient, preferably by intravenous injection, although parenteral administration is also suitable, at a hypotensive dosage level in a single dose of from 0.1 to 10 mg per kg of body weight, and the resulting transitory fall in blood pressure, if it occurs, indicates supranormal plasma renin levels.

In vitro methods which may be employed involve incubating a body fluid, preferably plasma, with a novel peptide of the present invention according to methods described in Boger et al., *J. Med. Chem.*, 1985, 28, 1779–1790.

The following are intended to exemplify the present invention, without, however, limiting it.

What is claimed is:

1. A peptide selected from the group consisting of:

N-(2,2,6,6-Tetramethylpiperidin-4-yl)Phe-His-ACHPA-Ile-NHCH$_2$(pyridin-4-yl)
N-(N-Ethylpiperidin-3-yl)Phe-His-ACHPA-Ile-NHCH$_2$(pyridin-4-yl)
N-(N-Ethylpiperidin-4-yl)Phe-His-ACHPA-Ile-NHCH$_2$(pyridin-4-yl)
N-(N-Phenylpiperidin-3-yl)Phe-His-ACHPA-Ile-NHCH$_2$(pyridin-4-yl)
N-(N-Benzylpiperidin-3-yl)Phe-His-ACHPA-Ile-NHCH$_2$(pyridin-4-yl)
N-[(Pyridin-2-yl)methyl]Phe-His-ACHPA-Ile-NHCH$_2$(pyridin-4-yl)
N-[(Pyridin-4-yl)methyl]Phe-His-ACHPA-Ile-NHCH$_2$(pyridin-4-yl)
N-[(Pyridin-4-yl)methyl]Phe-His-ACHPA-Ile-NHCH$_2$(pyridin-4-yl)
[N-[(N-Methylpyridin-2-yl)methyl]Phe-His-ACHPA-Ile-NHCH$_2$-(pyridin-4-yl)]$^+$Cl$^-$
N-[(Pyridin-2-yl)methyl]Phe-His-ACHPA-Ile-NHCH$_2$(pyridin-4-yl)
[N-(N-Methylpyridin-2-yl)Phe-His-ACHPA-Ile-NHCH$_2$-(pyridin-4-yl)]$^+$Cl$^-$
N-(Quinuclidin-3-yl)Phe-His-ACHPA-Ile-NHCH$_2$(pyridin-4-yl)
N-(Quinuclidin-4-yl)Phe-His-ACHPA-Ile-NHCH$_2$(pyridin-4-yl)
[N-(N-Methylquinuclidin-3-yl)Phe-His-ACHPA-Ile-NHCH$_2$-(pyridin-4-yl)]$^+$Cl$^-$
[N-(N-Methylquinuclidin-4-yl)Phe-His-ACHPA-Ile-NHCH$_2$-(pyridin-4-yl)]$^+$Cl$^-$
[N-(N-2-Hydroxy)ethylquinuclidin-4-yl)Phe-His-ACHPA-Ile-NHCH$_2$-(pyridin-4-yl)]$^+$Cl$^-$
N-(N-Carboxymethylquinuclidin-3-yl)Phe-His-ACHPA-Ile-NHCH$_2$-(pyridin-4-yl)]
[N-(N-Carboethoxymethylquinuclidin-3-yl)Phe-His-ACHPA-Ile-NHCH$_2$-(pyridin-4-yl)]$^+$Cl$^-$
N-Methyl-N-(quinuclidin-4-yl)Phe-His-ACHPA-Ile-NHCH$_2$-(pyridin-4-yl)
[N-(Methyl-N-(N-methylquinuclidin-4-yl)Phe-His-ACHPA-Ile-NHCH$_2$-(pyridin-4-yl)]$^+$Cl$^-$
N-Box-N-(quinuclidin-3-yl)Phe-His-ACHPA-Ile-NHCH$_2$(pyridin-4-yl)
N-(2-Benzylquinuclidin-3-yl)Phe-His-ACHPA-Ile-NHCH$_2$(pyridin-4-yl)
N-(Quinuclidin-3-yl)Phe-His-ACHPA-Ile-NHCH$_2$-(pyridin-4-yl)
N-(Quinuclidin-3-yl)Tyr(OMe)-His-ACHPA-Ile-NHCH$_2$(pyridin-4-yl)
N-(Quinuclidin-3-yl)HPhe-His-ACHPA-Ile-NHCH$_2$(pyridin-4-yl)
N-(Quinuclidin-3-yl)Phe-Nle-ACHPA-Ile-NHCH$_2$(pyridin-4-yl)
N-(Quinuclidin-3-yl)Phe-Thiz-ACHPA-Ile-NHCH$_2$(pyridin-4-yl)

N-(Quinuclidin-3-yl)Phe-Val-ACHPA-Ile-NHCH$_2$(pyridin-4-yl)
N-(Quinuclidin-3-yl)Phe-Phe-ACHPA-Ile-NHCH$_2$(pyridin-4-yl)
N-(Quinuclidin-3-yl)Tyr(OMe)-Nle-ACHPA-Ile-NHCH$_2$(pyridin-4-yl)
N-(Quinuclidin-3-yl)Nal-Nle-ACHPA-Ile-NHCH$_2$(pyridin-4-yl)
N-(Quinuclidin-3-yl)Phe-Nle-ACHPA-Leu-NHCH$_2$(pyridin-4-yl)
N-(Quinuclidin-3-yl)Phe-Nle-ACHPA-Phe-NHCH$_2$(pyridin-4-yl)
N-(Quinuclidin-3-yl)Phe-Nle-ACHPA-Lys-NHCH$_2$(pyridin-4-yl)
N-(Quinuclidin-3-yl)Phe-Nle-ACHPA-Orn-NHCH$_2$(pyridin-4-yl)
N-(Quinuclidin-3-yl)Phe-Nle-ACHPA-2(S)-methylbutyl
N-(Quinuclidin-3-yl)Phe-Nle-ACHPA-Ile-NHCH$_2$(pyridin-2-yl)
N-(Quinuclidin-3-yl)Phe-Nle-ACHPA-Leu-NHCH$_2$CH$_2$(imidazol-4-yl)
N-(Quinuclidin-3-yl)Phe-His-ACHPA-(N-methyl)Ile-NHCH$_2$(pyridin-4-yl)
N-(Quinuclidin-3-yl)Phe-His-ACHPA-Ile-NH(quinuclidin-3-yl)
[N-(Quniuclidin-3-yl)Phe-His-ACHPA-Ile-NH-(N-methylquinuclidin-3-yl)]$^+$OAc$^-$
N-(Quinuclidin-3-yl)Phe-His-Cal[CH(OH)CH$_2$]Val-NHCH$_3$
N-(Quinuclidin-3-yl)Phe-His-Cal[CH(OH)CH$_2$]Ala-NHCH$_3$
N-(Quinuclidin-3-yl)Phe-(NCl-Me)His-Cal[CH(OH)CH$_2$]Ala-NHCH$_3$
N-(Quinuclidin-3-yl)Phe-(N-Me)Nle-Cal[CH(OH)CH$_2$]Ala-NHCH$_3$
N-(Quinuclidin-3-yl)Nal-(N-Me)Nle-Cal[CH(OH)CH$_2$]Ala-NHCH$_3$
N-(Quinuclidin-3-yl)Nal-(N-Me)Nle-Cal[CH(OH)CH$_2$]Ala-NHCH$_2$(pyridin-4-yl)
N-(Quinuclidin-3-yl)Phe-His-Cal[CH(OH)CH$_2$]Ala-NHCH$_2$(pyridin-4-yl)
N-(Quinuclidin-4-yl)Phe-His-Cal[CH(OH)CH$_2$]Ala-NH-CH$_3$
[N-(N-Methylquinuclidin-3-yl)Phe-His-Cal[CH(OH)CH$_2$]Ala-NHCH$_3$]$^+$Cl$^-$
[N-(N-Methylquinuclidin-4-yl)Phe-His-Cal[CH(OH)CH$_2$]Ala-NHCH$_3$]$^+$Cl$^-$
[N-(N-Benzylquiniuclidin-3-yl)Phe-His-Cal[CH(OH)CH$_2$]Ala-NHCH$_3$]$^+$Cl$^-$
N-(N-Carboxymethylquinuclidin-3-yl)Phe-His-Cal[CH(OH)CH$_2$]Ala-NHCH$_3$]
[N-(N-Carboethoxyxymethylquinuclidin-3-yl)Phe-His-Cal[CH(OH)CH$_2$]Ala-NHCH$_3$]$^+$Cl$^-$
N-Methyl-N-(quinuclidin-4-yl)Phe-His-Cal-[CH(OH)CH$_2$]Ala-NHCH$_2$(pyridin-4-yl)
N-Methyl-N-(N-methylquinuclidin-4-yl)Phe-His-Cal[CH(OH)CH$_2$]Ala-NHCH$_3$ + Cl$_-$
N-Boc-N-(quinuclidin-3-yl)Phe-His-Cal-[CH(OH)CH$_2$]Ala-NHCH$_2$(pyridin-4-yl)
N-(2-Benzylquinuclidin-3-yl)Phe-His-Cal[CH(OH)CH$_2$]Ala-NHCH$_2$(pyridin-4-yl)
N-(Quinuclidin-3-yl)Phe-His-ACHPA-N(CH$_2$CH$_3$)CH$_2$CH$_2$N(CH$_2$CH$_3$)$_2$
N-(Quinuclidin-3-yl)Phe-His-ACHPA-N(CH$_2$CH$_3$)CH$_2$CH$_2$N(CH$_2$CH$_3$)$_2$O
N-(Quinuclidin-3-yl)Phe-His-ACHPA-N(CH$_2$CH$_3$)CH(OH)CH$_2$N(CH$_2$CH$_2$)$_2$O
[N-(Quinuclidin-3-yl)Phe-His-ACHPA-(CH$_2$CH$_3$)CH$_2$CH(OH)CH$_2$N(CH$_3$)(CH$_2$CH$_2$-)$_2$O]$^+$Cl$^-$
N-(Quinuclidin-3-yl)Phe-His-ACHPA-N(CH$_2$CH$_3$)CH$_2$(pyridin-4-yl)
N-(Quinuclidin-3-yl)Phe-His-ACHPA-N(CH$_2$CH$_3$)CH$_2$CH$_2$(pyridin-4-yl)
N-(Quinuclidin-3-yl)Phe-His-ACHPA-N(CH$_2$CH$_2$)$_2$O
N-(Quinuclidin-3-yl)Phe-His-ACHPA-N(CH$_2$CH$_3$)-2(S)-methylbutyl
N-(Quinuclidin-3-yl)Phe-His-ACHPA-N(CH$_2$CH$_3$)(CH$_2$)$_3$CH$_3$
N-(Quinuclidin-3-yl)Phe-His-ACHPA-N(CH$_2$CH$_3$)(2,2,6,6-tetramethylpiperidin-4-yl)
N-(Quinuclidin-3-yl)Phe-His-ACHPA-N[(CH$_2$)$_4$-]CH$_2$CH(−)N(CH$_2$CH$_3$)$_2$
N-(Quinuclidin-3-yl)Phe-His-ACHPA-NH(quinuclidin-3-yl)
[N-(Quinuclidin-3-yl)Phe-His-ACHPA-NH(N-methylquinuclidin-3-yl)]$^+$OAc$^-$
N-(Quinuclidin-3-yl)Phe-His-norACHPA-O-iPr
N-(Quinuclidin-3-yl)Phe-His-norACHPA-O-2(S)-methylbutyl
[N-(N-Benzylquinuclidin-3-yl)Phe-His-norACHPA-O-2(S)-methylbutyl]$^+$ $^-$OCOPh
N-(N-Carboxymethylquinuclidin-3-yl)Phe-His-norACHPA-O-iPr
N-(2,2,6,6-tetramethylpiperidin-4-yl)Phe-His-norACHPA-O-iPr
N-[N-(Quinuclidin-3-yl)Phe-His-]-2(S)-amino-1-cyclohexyl-3(S)-hydroxy-6-methylheptane
N-[N-(Quinuclidin-3-yl)Phe-His-]-2(S)-amino-1-cyclohexyl-3(S), 4(R)-dihydroxy-6-methylheptane
[N-[N-(N-methylquinuclidin-3-yl)Phe-His-]-2(S)-amino-1-cyclohexyl-3(S), 4(R)-dihydroxy-6-methylheptane]$^+$OAc$^-$
N-[N-(Quinuclidin-3-yl)Phe-His-]-2(S)-amino-1-cyclohexyl-3(R), 4(S)-dihydroxy-5-methylheptane
N-[N-(Quinuclidin-3-yl)Phe-His-]-4(S)-amino-1-cyclohexylmethyl-2(S), 3(R)-dihydroxy-1-(isopropylsulfonyl)pentane
N-[N-(Quinuclidin-3-yl)Phe-His-]-4(S)-amino-1-cyclohexylmethyl-2(S), 3(R)-dihydroxy-1-(morpholin-1-yl)pentane
[N-[N-(N-methylquinuclidin-3-yl)Phe-His-]-4(S)-amino-5-cyclohexylmethyl-2(R), 3(R)-dihydroxy-1-(morpholin-1-yl)pentane]$^+$OAc$^-$
[N-(N-Benzylquinuclidin-3-yl)Phe-ACHPA-Ile-NHCH$_2$(pyridin-4-yl)]$^+$OAc$^-$
N-(N-Benzylquinuclidin-3-yl)Phe-ACHPA-Ile-NHCH$_2$(pyridin-4-yl)
[N-(N-Methyl-2-benzylquinuclidin-3-yl)Phe-ACHPA-Ile-NHCH$_2$(pyridin-4-yl)]$^+$OAc$^-$
[N-(2-benzylquinuclidin-3-yl)His-ACHPA-Ile-NHCH$_2$(pyridin-4-yl)
[N-(2-benzylquinuclidin-3-yl)Nle-ACHPA-Ile-NHCH$_2$(pyridin-4-yl)
[N-(N-Benzylquinuclidin-3-yl)Nle-ACHPA-Ile-NHCH$_2$(pyridin-4-yl)]$^+$OAc$^-$
N-(2-Benzylquinuclidin-3-yl)His-Cal[CH(OH)CH$_2$]Ala-NHCH$_2$(pyridin-4-yl)
N-(2-Benzylquinuclidin-3-yl)His-Cal[CH(OH)CH$_2$]Ala-NHCH$_3$
N-(2-Benzylquinuclidin-3-yl)Nle-Cal[CH(OH)CH$_2$]Ala-NHCH$_3$ and
[N-(N-Methyl-2-benzylquinuclidin-3-yl)His-Cal[CH(OH)CH$_2$]Ala-NHCH$_2$(pyridin-4-yl)]$^+$OAc$^-$ 2. A pharmaceutical composition for renin-associated hypertension or congestive heart failure comprising a pharmaceutical carrier and a therapeutically-effective amount of a peptide according to claim 1.

3. A pharmaceutical composition according to claim 2, also comprising an adjuvant.

4. A pharmaceutical composition according to claim 2, also comprising one compound selected from the group consisting of:
(1-(2-exobicyclo[2.2.1]-hept-2-ylphenoxy)-3-[(1-methylethyl)-amino]-2-propanol HCl) (bornaprolol);
(o-[2-hydroxy-3-[(2-indol-3-yl-1,1-dimethylethyl)amino]propoxy]benzonitrile HCl) (bucindolol);
(a-[(tert.butylamino)methyl]-7-ethyl-2-benzofuranmethanol) (bufuralol);
(3-[3-acetyl-4-[3-(tert.butylamino)-2-hydroxypropyl]-phenyl]-1,1-diethylurea HCl) (celiprolol);
((±)-2-[2-[3-[(1,1-dimethylethyl)amino]-2-hydroxypropoxy]phenoxy]-N-methylacetamide HCl) (cetamolol);
(2-benzimidazolyl-phenyl(2-isopropylaminopropanol));
((±)-3'-acetyl-4'-(2-hydroxy-3-isopropylaminopropoxy)acetanilide HCl) (diacetolol);
(methyl-4-[2-hydroxy-3-[(1-methylethyl)aminopropoxy]]benzenepropanoate HCl) (esmolol);
(erythro-DL-1-(7-methylindan-4-yloxy)-3-isopropylaminobutan-2-ol);
(1-(tert.butylamino)-3-[O-(2-propynyloxy)phenoxy]-2-propanol (pargolol);
(1-(tert.butylamino)-3-[o-(6-hydrazino-3-pyridazinyl)phenoxy]-2-propanol diHCl) (prizidilol);
((−)-2-hydroxy-5-[(R)-1-hydroxy-2-[(R)-(1-methyl-3-phenylpropyl)amino]ethyl]benzamide);
(4-hydroxy-9-[2-hydroxy-3-(isopropylamino)-propoxy]-7-methyl-5H-furo[3,2-g][1]-benzopyran-5-one) (iprocrolol);
((−)-[5-(tert.butylamino)-2-hydroxypropoxy]-3,4-dihydro-1-(2H)-naphthalenone HCl) (levobunolol);
(4-(2-hydroxy-3-isopropylamino-propoxy)-1,2-benzisothiazole HCl);
(4-[3-(tert.butylamino)-2-hydroxypropoxy]-N-methylisocarbostyril HCl);
Diuretics: acetazolamide; amiloride; bendroflumethiazide; benzthiazide; bumetanide; chlorothiazide; chlorthalidone; cyclothiazide; ethacrynic acid; furosemide; hydrochlorothiazide; hydroflumethiazide; indacrinone (racemic mixture, or as either the (+) or (−) enantiomer alone, or a manipulated ratio, e.g., 9:1 of said enantiomers, respectively); metolazone; methylclothiazide; muzolimine; polythiazide; quinethazone; sodium ethacrynate; sodium nitroprusside; spironolactone; ticrynafen; triamterene; trichlormethiazide;
α-Adrenergic Blocking Agents: dibenamine; phentolamine; phenoxybenzamine; prazosin; tolazoline;
β-Adrenergic Blocking Agents: atenolol; metoprolol; nadolol; propranolol; timolol;
((±)-2-[3-(tert-butylamino)-2-hydroxypropoxy]-2-furananilide) (ancarolol);
(2-acetyl-7-(2-hydroxy-3-isopropylaminopropoxy)benzofuran HCl) (befunolol);
((±)-1-(isopropylamino)-3-(p-(2-cyclopropylmethoxyethyl)-phenoxy)-2-propranol HCl) (betaxolol);
(1-[(3,4-dimethoxyphenethyl)amino]-3-(m-tolyloxy)-2-propanol HCl) (bevantolol);
((±)-1-(4-((2-isopropoxyethoxy)methyl)phenoxy)-3-isopropylamino-2-propanol)fumarate) (bisoprolol);
(4-(2-hydroxy-3-[4-(phenoxymethyl)-piperidino]-propoxy)-indole);
(carbazolyl-4-oxy-5,2-(2-methoxyphenoxy)-ethylamino-2-propanol);
(1-((1,1-dimethylethyl)amino)-3-((2-methyl-1H-indol-4-yl)oxy)-2-propanol benzoate) (bopindolol);
((±)-N-2-[4-(2-hydroxy-3-isopropyl aminopropoxy)-phenyl]ethyl-N'-isopropylurea) (pafenolol);
(3-[[(2-trifluoroacetamido)ethyl]amino]-1-phenoxypropan-2-ol);
(N-(3-(o-chlorophenoxy)-2-hydroxypropyl)-N'-(4'-chloro-2,3-dihydro-3-oxo-5-pyridazinyl)ethylenediamine);
((±)-N-[3-acetyl-4-[2-hydroxy-3-[(1-methylethyl)amino]propoxy]phenyl]butanamide) (acebutolol);
((±)-4'-[3-(tert-butylamino)-2-hydroxypropoxy]spiro[cyclohexane-1,2'-indan]-1'-one) (spirendolol);
(7-[3-[[2-hydroxy-3-[(2-methylindol-4-yl)oxy]propyl]amino]butyl]thiophylline) (teoprolol);
((±)-1-tert.butylamino-3-(thiochroman-8-yloxy)-2-propanol) (tertatolol);
((±)-1-tert.butylamino-3-(2,3-xylyloxy)-2-propanol HCl) (xibenolol);
(8-[3-(tert.butylamino)-2-hydroxypropoxy]-5-methylcoumarin) (bucumolol);
(2-(3-(tert.butylamino)-2-hydroxy-propoxy)benzonitrile HCl) (bunitrolol);
((±)-2'-[3-(tert-butylamino)-2-hydroxypropoxy-5'-fluorobutyrophenone) (butofilolol);
(1-(carbazol-4-yloxy)-3-(isopropylamino)-2-propanol) (carazolol);
(5-(3-tert.butylamino-2-hydroxy)propoxy-3,4-dihydrocarbostyril HCl) (carteolol);
(1-(tert.butylamino)-3-(2,5-dichlorophenoxy)-2-propanol) (cloranolol);
(1-(inden-4(or 7)-yloxy)-3-(isopropylamino)-2-propanol HCl) (indenolol);
(1-isopropylamino-3-[(2-methylindol-4-yl)oxy]-2-propanol) (mepindolol);
(1-(4-acetoxy-2,3,5-trimethylphenoxy)-3-isopropylaminopropan-2-ol) (metipranolol);
(1-(isopropylamino)-3-(o-methoxyphenoxy)-3-[(1-methylethyl)amino]-2-propanol) (moprolol);
((1-tert.butylamino)-3-[(5,6,7,8-tetrahydro-cis-6,7-dihydroxy-1-naphthyl)oxy]-2-propanol) (nadolol);
((S)-1-(2-cyclopentylphenoxy)-3-[(1,1-dimethylethyl)amino]-2-propanol sulfate (2:1)) (penbutolol);
(4'-[1-hydroxy-2-(amino)ethyl]methanesulfonanilide) (sotalol);
(2-methyl-3-[4-(2-hydroxy-3-tert.butylaminopropoxy)-phenyl]-7-methoxy-isoquinolin-1-(2H)-one);
(1-(4-(2-(4-fluorophenyloxy)ethoxy)phenoxy)-3-isopropylamino-2-propanol HCl);
((−)-p-[3-[(3,4-dimethoxyphenethyl)amino]-2-hydroxypropoxy]-β-methylcinnamonitrile) (pacrinolol);
((±)-2-(3'-tert.butylamino-2'-hydroxypropylthio)-4-(5'-carbamoyl-2'-thienyl)thiazole HCl) (arotinolol);
((±)-1-[p-[2-(cyclopropylmethoxy)ethoxy]phenoxy]-3-(isopropylamino)-2-propanol) (cicloprolol);
((±)-1-[(3-chloro-2-methylindol-4-yl)oxy]-3-[(2-phenoxyethyl)amino]-2-propanol) (indopanolol);
((±)-6-[[2-[[3-(p-butoxyphenoxy)-2-hydroxypropyl]amino]ethyl]amino]-1,3-dimethyluracil) (pirepolol);
(4-(cyclohexylamino)-1-(1-naphtholenyloxy)-2-butanol);
(1-phenyl-3-[2-[3-(2-cyanophenoxy)-2-hydroxypropyl]aminoethyl]hydantoin HCl);
(3,4-dihydro-8-(2-hydroxy-3-isopropylaminopropoxy)-3-nitroxy-2H-1-benzopyran) (nipradolol);
α-and β-Adrenergic Blocking Agents:

((±)-1-tert-butylamino-3-[o-[2-(3-methyl-5-isoxazolyl)vinyl]phenoxy]-2-propanol) (isoxaprolol);
(1-isopropylamino-3-(4-(2-nitroxyethoxy)phenoxy)-2-propanol HCl);
(4-hydroxy-α-[[3-(4-methoxyphenyl)-1-methylpropyl]aminomethyl]-3-(methylsulfinyl)-benzmethanol HCl) (sulfinalol);
(5-[1-hydroxy-2-[[2-(o-methoxyphenoxy)ethyl]amino]ethyl]-2-methylbenzenesulfonamide HCl);
(5-[1-hydroxy-2-[(1-methyl-3-phenylpropyl)amino]ethyl]-salicylamide HCl) (labetalol);
(1-((3-chloro-2-methyl-1H-indol-4-yl)oxy)-3-((2-phenoxyethyl)amino)-2-propanol-hydrogenmalonate) (ifendolol);
(4-(2-hydroxy-3-[(1-methyl-3-phenylpropyl)amino]propoxy)benzeneacetamide);
(1-[3-[[3-(1-naphthoxy)-2-hydroxypropyl]-amino]-3,3-dimethyl-propyl]-2-benzimidazolinone);
(3-(1-(2-hydroxy-2-(4-chlorophenylethyl)-4-piperidyl)-3,4-dihydroxy)quinoxolin-2(1H)-one;
CNS-Acting Agents: clonidine; methyldopa;
Adrenergic Neuron Blocking Agents: guanethidine; reserpine and other rauwolfia alkaloids such as rescinnamine;
Vasodilators: diazoxide; hydralazine; minoxidil;
Angiotensin I Converting Enzyme Inhibitors:
1-(3-mercapto-2-methyl-1-oxopropyl)-L-proline (captopril);
(1-(4-ethoxycarbonyl-2,4(R,R)-dimethylbutanoyl)indoline-2(S)-carboxylic acid);
(2-[2-[[1-(ethoxycarbonyl)-3-phenyl-propyl]amino]-1-oxopropyl]-1,2,3,4-tetrahydro-3-isoquinoline carboxylic acid);
((S)-1-[2-[[1-(ethoxycarbonyl)-3-phenylpropyl]amino]-1-oxopropyl]octahydro-1H-indole-2-carboxylic acid HCl);
(N-cyclopentyl-N-(3-(2,2-dimethyl-1-oxopropyl)thiol-2-methyl-1-oxopropyl)glycine) (pivalopril);
((2R,4R)-2-(2-hydroxyphenyl)-3-(3-mercaptopropionyl)-4-thiazolidinecarboxylic acid);
(1-(N-[1(S)-ethoxycarbonyl-3-phenylpropyl]-(S)-alanyl)-cis,syn-octahydroindol-2(S)-carboxylic acid HCl);
((−)-(S)-1-[(S)-3-mercapto-2-methyl-1-oxopropyl]indoline-2-carboxylic acid);
([1(S),4S]-1-[3-(benzoylthio)-2-methyl-1-oxopropyl]-4-phenylthio-L-proline;
(3-([1-ethoxycarbonyl-3-phenyl-(1S)-propyl]amino)-2,3,4,5-tetrahydro-2-oxo-1-(3S)-benzazepine-1-acetic acid HCl);
(N-(2-benzyl-3-mercaptopropanoyl)-S-ethyl-L-cysteine) and the S-methyl analogue;

(N-(1(S)-ethoxycarbonyl-3-phenylpropyl)-L-alanyl-L-proline maleate) (enalapril);
N-[1-(S)-carboxy-3-phenylpropyl]-L-alanyl-1-proline;
$N^2$-[1-(S)-carboxy-3-phenylpropyl]-L-lysyl-L-proline (lysinopril);
Calcium Channel Blockers:
α-[3-[[2-(3,4-dimethoxyphenyl)ethyl]methylamino]propyl]-3,4-dimethoxy-α-(1-methylethyl)benzeneacetonitrile (verapamil);
1,4-dihydro-2,6-dimethyl-4-(2-nitrophenyl)-3,5-pyridinedicarboxylic acid dimethyl ester (nifedipine);
2-(2,2-dicyclohexylethyl)piperidine (perhexiline);
N-(1-methyl-2-phenylethyl)-phenylbenzenepropanamine (prenylamine);
3-(aminosulfonyl)-4-chloro-N-(2,3-dihydro-2-methyl-1H-indol-1-yl)benzamide (indapamide);
(2'-(2-diethylaminoethoxy)-3-phenylpropiophenone (etafenone);
(4-[4,4-bis-(4-fluorophenyl)butyl]-N-(2,6-dimethylphenyl)-1-piperazineacetamide) (lidoflazine);
(2-(N-benzyl-N-methylamino)ethylmethyl-2,6-dimethyl-4-(m-nitrophenyl)-1,4-dihydro-3,5-pyridinedicarboxylate HCl) (nicardipine);
(N-(3,4-dimethoxyphenethyl)-2-(3,4-dimethoxyphenyl)-N-methyl-m-dithiane-2-propylamine-1,1,3,3-tetraoxide) (tiapamil);
(5,6-dimethoxy-2-(3-[(a-(3,4-dimethoxy)phenylethyl)-methylamino]propyl)phthalimidine) (falipamil);
(β-[(2-methylpropoxy)methyl]-N-phenyl-N-phenylmethyl-1-pyrrolidineethanamine HCl monohydrate) (bepridil);
((+)-cis-3-(acetyloxy)-5-[2-(dimethylamino)ethyl]-2,3-dihydro-2-(4-methoxyphenyl)-1,5-benzothiazepin-4-(5H)-one) (diltiazem);
((E)-1-[bis-(p-fluorophenyl)methyl]-4-cinnamylpiperazine di HCl) (flunarizine);
(5-[(3,4-dimethoxyphenethyl)methylamino]-2-isopropyl-2-(3,4,5-trimethoxyphenyl)valeronitrile (gallopamil);
(ethylmethyl(2,3-dichlorophenyl)-1,4-dihydro-2,6-dimethyl-3,5-pyridinedicarboxylate (felodipine);
(isopropyl-2-methoxyethyl-1,4-dihydro-2,6-dimethyl-4-(3-nitrophenyl)-3,5-pyridinecarboxylate) (nimodipine);
(3-ethyl-5-methyl-1,4-dihydro-2,6-dimethyl-4-(3-nitrophenyl)-3,5-pyridine-dicarboxylate) (nitrendipine); and
Other Antihypertensive Agents: aminophylline; cryptenamine acetates and tannates; deserpidine; meremethoxylline procaine; pargyline; trimethaphan camsylate; and the like, as well as admixtures and combinations thereof.

* * * * *